US005651785A

United States Patent [19]
Abela et al.

[11] Patent Number: 5,651,785
[45] Date of Patent: Jul. 29, 1997

[54] OPTICAL FIBER CATHETER AND METHOD

[75] Inventors: George S. Abela, Wellesley; Stephan E. Friedl, Watertown; Eric D. Mathews, North Attleboro, all of Mass.

[73] Assignees: Abela Laser Systems, Inc., E. Lansing, Mich.; University of Florida Research Foundation, Inc., Gainesville, Fla.

[21] Appl. No.: 474,152

[22] Filed: Jun. 7, 1995

Related U.S. Application Data

[63] Continuation-in-part of Ser. No. 123,207, Sep. 20, 1993, Pat. No. 5,464,404, and a division of Ser. No. 394,763, Sep. 20, 1993.

[51] Int. Cl.⁶ .................................................. A61B 17/36
[52] U.S. Cl. .................................................. 606/15
[58] Field of Search ............................. 606/8, 10, 11, 606/12, 13, 14, 15, 16, 41; 128/668, 673, 693

[56] References Cited

U.S. PATENT DOCUMENTS

| | | |
|---|---|---|
| 4,723,936 | 2/1988 | Buchbinder et al. . |
| 4,740,047 | 4/1988 | Abe et al. . |
| 4,758,222 | 7/1988 | McCoy . |
| 4,765,330 | 8/1988 | Bach . |

(List continued on next page.)

FOREIGN PATENT DOCUMENTS

| | | |
|---|---|---|
| 9402076 | 2/1994 | WIPO . |
| 9402077 | 2/1994 | WIPO . |

OTHER PUBLICATIONS

Paper entitled "AngeLase laser Ablation System".
"Development and Early Clinical Applications of a Lateral-aiming Laser Probe", Daijo Hashimoto, Lasers in Medical Science, vol. 2:25 1987, pp. 25–28.

*Primary Examiner*—Angela D. Sykes
*Assistant Examiner*—Sony Harris-Oguya
*Attorney, Agent, or Firm*—William L. Feeney; Kerkam, Stowell, Kondracki & Clarke, P.C.

[57] ABSTRACT

A catheter uses a steerable outer catheter with an inner catheter rotatable and extendable with respect to the outer catheter. The outer catheter may be positioned within a patient's heart and a portion of the outer catheter may provide movement like that of a windshield wiper by manipulation of a spring. By combining the windshield wiper type movement with the extension and rotation of the inner catheter relative to the outer catheter, a large area within a patient's heart may be readily mapped for conduction tissue and be subjected to laser ablation if appropriate. Various configurations provide flexibility in relatively positioning of windows used to apply laser energy and ring electrodes used to sense conduction tissue. Some embodiments provide only laser ablation (no mapping).

9 Claims, 14 Drawing Sheets

U.S. PATENT DOCUMENTS

| | | |
|---|---|---|
| 4,784,132 | 11/1988 | Fox et al. |
| 4,785,815 | 11/1988 | Cohen. |
| 4,800,876 | 1/1989 | Fox et al. |
| 4,800,890 | 1/1989 | Cramer. |
| 4,848,336 | 7/1989 | Fox et al. |
| 4,850,351 | 7/1989 | Herman et al. |
| 4,852,280 | 8/1989 | Wood. |
| 4,860,743 | 8/1989 | Abela. |
| 4,862,886 | 9/1989 | Clarke et al. |
| 4,913,142 | 4/1990 | Kittrell et al. |
| 4,921,482 | 5/1990 | Hammerslag et al. |
| 4,940,064 | 7/1990 | Desai. |
| 4,955,882 | 9/1990 | Hakky. |
| 4,985,028 | 1/1991 | Isner et al. |
| 4,997,431 | 3/1991 | Isner et al. |
| 4,998,916 | 3/1991 | Hammerslag et al. |
| 5,037,391 | 8/1991 | Hammerslag et al. |
| 5,041,108 | 8/1991 | Fox et al. |
| 5,041,109 | 8/1991 | Abela. |
| 5,061,265 | 10/1991 | Abela et al. |
| 5,083,565 | 1/1992 | Parins. |
| 5,104,393 | 4/1992 | Isner et al. |
| 5,106,386 | 4/1992 | Isner et al. |
| 5,108,368 | 4/1992 | Hammerslag et al. |
| 5,112,304 | 5/1992 | Barlow et al. |
| 5,114,402 | 5/1992 | McCoy. |
| 5,114,403 | 5/1992 | Clarke et al. |
| 5,125,395 | 6/1992 | Adair. |
| 5,125,895 | 6/1992 | Buchbinder et al. |
| 5,135,517 | 8/1992 | McCoy. |
| 5,154,501 | 10/1992 | Svenson et al. |
| 5,172,699 | 12/1992 | Svenson et al. |
| 5,228,299 | 7/1993 | Harrington et al. |
| 5,263,977 | 11/1993 | Adams et al. |
| 5,281,212 | 1/1994 | Savage et al. |
| 5,290,277 | 3/1994 | Vercimak et al. |
| 5,338,299 | 8/1994 | Barlow. |
| 5,354,294 | 10/1994 | Chou. |
| 5,366,456 | 11/1994 | Rink et al. |
| 5,368,564 | 11/1994 | Savage. |

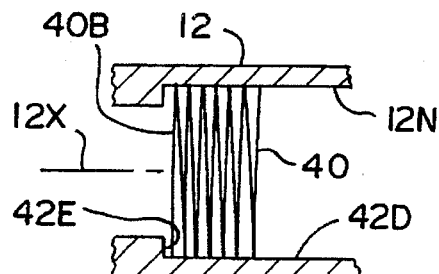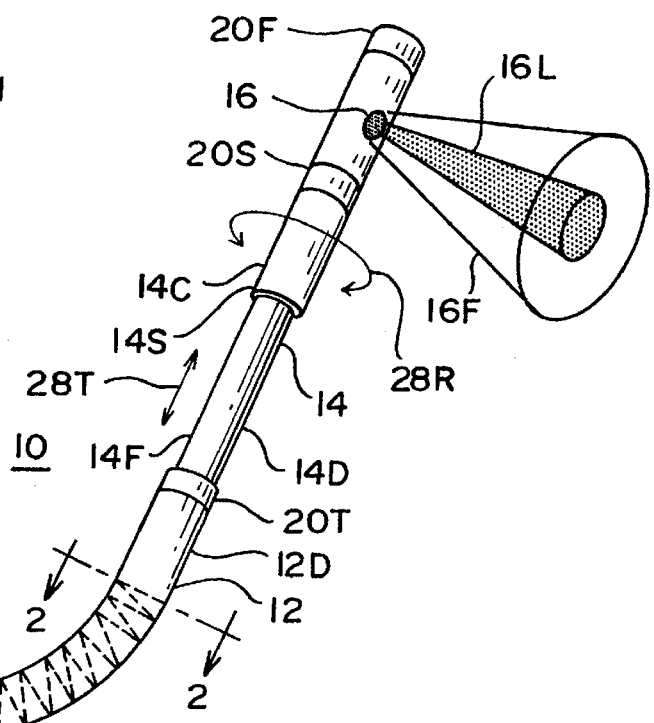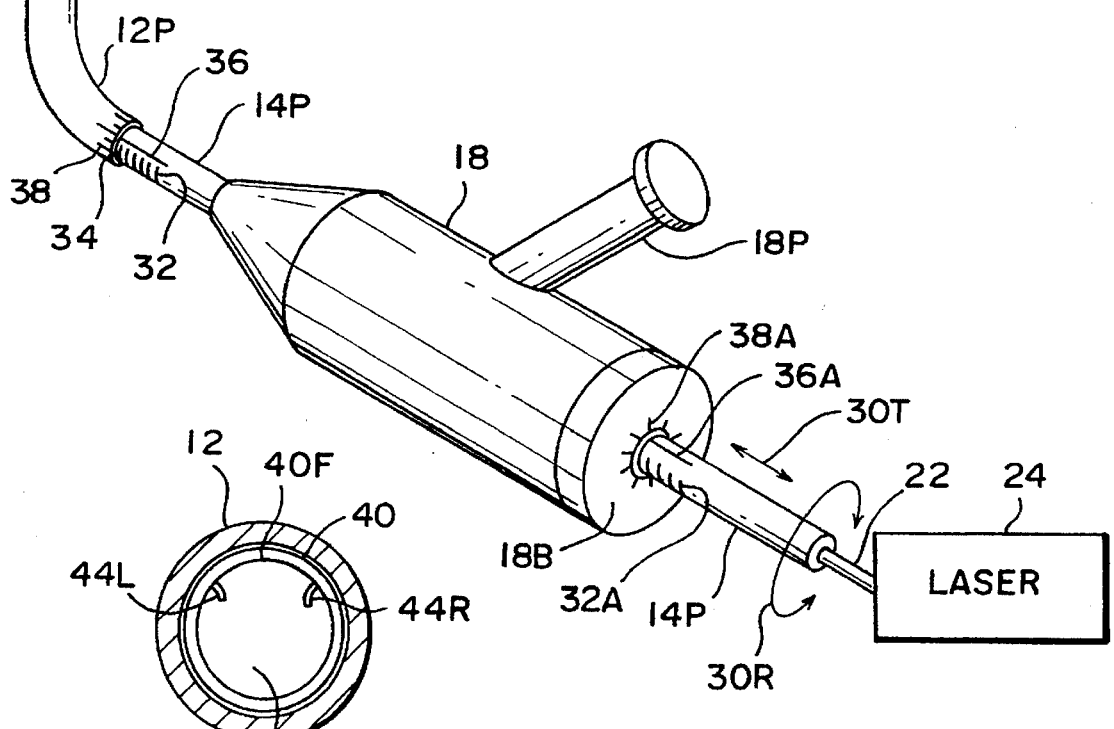
FIG. 3
FIG. 1
FIG. 2

OPTICAL FIBER CATHETER AND METHOD

CROSS-REFERENCE TO RELATED APPLICATIONS

This application is a continuation-in-part of U.S. patent application Ser. No. 08/123,207 filed Sep. 20, 1993 now U.S. Pat. No. 5,464,404 in the names of Abela, Friedl, and Mathews, the inventors herein. A divisional application Ser. No. 08/394,763 of that application was filed Sep. 20, 1993. Another continuation-in-part of U.S. patent application Ser. No. 08/123,207 is being filed concurrently herewith in the names of Abela, Friedl, and Mathews and titled MAPPING CATHETER AND METHOD. Another continuation-in-part of U.S. patent application Ser. No. 08/123,207 is being filed concurrently herewith in the names of Abela, Friedl, Mathews and Bowden and titled CARDIAC CATHETER ANCHORING AND METHOD. All of the referenced applications including their claims, drawings and text as originally filed and all amendments made prior to the present filing date are hereby incorporated by reference.

BACKGROUND OF THE INVENTION

This invention relates to an apparatus and method for treating cardiac or similar conditions in a patient. More specifically, this invention relates to mapping of, and application of laser energy, to the tissues of a patient.

The use of laser beams for treatment of medical conditions has been well known. Various devices have also been developed for application of laser energy to tissue inside of a patient.

In order to provide laser energy to tissue within a patient for such purposes as ablation of plaque from the walls of a blood vessel, a technique is required which can accurately apply the laser energy to the tissue. Various problems have been encountered in application of laser energy to tissues of a patient. For example, the laser passing through a glass window may cause the build up of burnt tissue or burnt blood cells at and around the point at which the laser exits the glass window. This black, carbonized material would in turn absorb the laser energy before it could strike the tissue and would at least partially block the laser energy from striking the tissues of the patient. This may damage the laser catheter device itself.

George S. Abela and Stephan E. Friedl, both among the inventors of the present application, obtained U.S. patent No. 5,061,265 on Oct. 29, 1991, entitled "LASER TREATMENT APPARATUS AND METHOD", hereby incorporated by reference. That patent discloses a dual hood arrangement whereby laser energy passes out through an inner hood having a window of transparent material and passes through an opening of an outer hood. By supplying pressurized flushing solution to within the outer hood, the flushing solution maintains the inner hood relatively clear of burned materials and flows out the same opening as the laser energy.

Among other prior patents, U.S. Pat. No. 4,860,743, issued Aug. 29, 1989 to George S. Abela and U.S. Pat. No. 5,041,109, issued Aug. 20, 1991 to George S. Abela, both disclose various laser catheters for treatment of cardiac conditions. Those patents, both of which are hereby incorporated by reference, disclose the use of electrode rings on the catheters for detection of conduction tissue. Such rings are also discussed in the Abela et al '265 patent mentioned above. The electrode rings allow one to locate tissue which is to be treated.

Although the above and various other designs of catheters have been quite useful, they have often been subject to one or more of several limitations or disadvantages. For example, positioning of the catheters within the patient has often been difficult and/or very time-consuming. The problem of positioning of the catheter for proper application of the laser energy is evident in treatment of arrhythmia conditions. Use of electrodes for mapping the conduction tissues of the heart has often been less efficient than desirable. The prior arrangements have often been less than satisfactory for AV (atrial-ventricular) nodal ablation. Generally, the fixed relationship between the laser beam and the electrodes has reduced flexibility in treating various conditions.

Among other problems with catheters in which flushing solution is used, body fluids may undesirably enter into the catheter through the port from which flushing solution is supplied during any halt in the supply of the flushing solution. That is, if one wishes to halt the supply of flushing solution temporarily, blood or other bodily fluids may enter into the port and the associated passage or channel used to supply the flushing solution.

OBJECTS AND SUMMARY OF THE INVENTION

Accordingly, it is a primary object of the present invention to provide new and improved catheter designs and an associated method.

A more specific object of the present invention is to provide a catheter design which has a great deal of flexibility and adaptability in positioning.

A further object of the present invention is to provide a catheter allowing for variations in the relationship between the window used to supply laser energy and other parts of the catheter.

A further object of the present invention is to provide for the stabilization of the position of a large part of the catheter, while allowing variations in positioning of a window used to supply laser energy.

Yet another object of the present invention is to provide various different relationships between a window and electrodes used to sense conduction tissue.

A still further object of the present invention is to provide a technique for minimizing the ability of bodily fluids to enter into the catheter.

Yet another object of the present invention is to provide a steering device for a catheter.

The above and other objects of the present invention which will be more readily understood when the following detailed description is considered in conjunction with the accompanying drawings are realized by an apparatus for patient treatment having an outer catheter with a proximal end and a distal end having at least a first passage extending lengthwise therein. (As used herein, "patient treatment" shall include diagnosis of patient conditions as well as application of techniques to improve patient conditions.) An inner catheter is disposed at least partly in the first passage and has a proximal end and a distal end. The inner catheter has a side wall, a window in the side wall, and an optical fiber having a tip. The window is positioned such that light may pass between the tip and a light communicating part of the window. (As used herein, a "window" shall include both an opening through which light may pass as well as a light passage with material which is transparent to light.) The inner catheter has an extending portion extendable out the distal end of the outer catheter by a variable amount. Lengthwise offset first and second electrodes are used. The first electrode is mounted on an external surface of the side wall and the second electrode is mounted either on the external surface of the side wall or an external surfaces of the outer catheter.

The first and second electrodes are operable for detecting the presence of conductive cardiac tissue. A steering means is used for steering the outer catheter. The inner catheter is rotatable relative to the outer catheter.

In one embodiment, the second electrode is on the external surface of the side wall and a third electrode is disposed on the external surface of the outer catheter.

In another embodiment, the second electrode is on an external surface of the outer catheter such that extension of the inner catheter relative to the outer catheter varies the distance between the first and second electrodes.

The first and second electrodes have contact surfaces which are limited to an angular range excluding at least a back part of the side wall radially opposite the window. The first and second electrodes are respectively first and second rings and a back part of each ring is covered by insulating material in a specific arrangement.

One embodiment uses a third electrode with the second and third electrodes both mounted on the external surface of the side wall for detecting the presence of conductive cardiac tissue. That embodiment may more specifically include a fourth electrode also mounted on the external surface of the side wall for detecting the presence of conductive cardiac tissue.

In one aspect of the present invention, the window is lengthwise outside a zone including the first and second electrodes and a space therebetween.

In one embodiment or aspect of the present invention, the first electrode may have a contact surface which completely surrounds the window.

In another embodiment or aspect of the present invention, the window may have at least a first valve member for selectively opening and closing the window.

One embodiment of the present invention may use a second window in the side wall which is lengthwise offset from the previously mentioned or first window. The optical fiber is movable between a position in which light passes between the tip and the first window and a position in which light passes between the tip and the second window.

The optical fiber is operable to carry laser energy to cardiac tissues of a patient. The window is more specifically an opening for passage of light and flushing solution.

The steering means in one embodiment is disposed within a second passage in the outer catheter.

In another embodiment, the steering means includes a coil spring mounted to the distal end of the outer catheter, two control lines attached to the coil, and a control means for bending the coil spring by manipulating the control lines.

The present invention may also be described as an apparatus for patient treatment including:
 an outer catheter having a proximal end and a distal end having at least a first passage extending lengthwise therein;
 an inner catheter movably disposed at least partly in the first passage and having a proximal end and a distal end, the inner catheter having a side wall, a first window in the side wall, and an optical fiber having a tip, the first window positioned such that light may pass between the tip and a light communicating part of the first window, the inner catheter having an extending portion extendable out the distal end of the outer catheter;
 lengthwise offset first and second electrodes, the first electrode mounted on an external surface of the side wall and the second electrode mounted on a surface selected from the group consisting of: the external surface of the side wall and an external surface of the outer catheter, the first and second electrodes operable for detecting the presence of conductive cardiac tissue; and
 a steering means for steering the outer catheter; and wherein the steering means includes a coil spring mounted near the distal end of the outer catheter, two control lines attached to the coil, and a control means for bending the coil spring by manipulating the control lines.

The present invention may alternately be described as an apparatus for patient treatment including:
 an outer catheter having a proximal end and a distal end having at least a first passage extending lengthwise therein;
 an inner catheter disposed at least partly in the first passage and having a proximal end and a distal end, the inner catheter having a side wall, a first window in the side wall, and an optical fiber having a tip, the first window positioned such that light may pass between the tip and a light communicating part of the first window, the inner catheter having an extending portion extendable out the distal end of the outer catheter;
 lengthwise offset first and second electrodes, the first electrode mounted on an external surface of the side wall and the second electrode mounted on a surface selected from the group consisting of: the external surface of the side wall and an external surface of the outer catheter, the first and second electrodes operable for detecting the presence of conductive cardiac tissue; and
 a steering means for steering the outer catheter; and wherein the inner catheter is rotatable relative to the outer catheter.

The present invention may alternately be described as an apparatus for patient treatment including:
 a housing with a side wall;
 a first window in the side wall;
 an optical fiber having a tip, the first window positioned such that light may pass between the tip and a light communicating part of the first window; and
 lengthwise offset first and second electrodes mounted to the side wall and operable for detecting the presence of conductive cardiac tissue; and
 wherein the side wall includes first and second portions on which the first and second windows are respectively disposed, and the first portion is movable relative to the second portion to vary the distance between the first and second electrodes.

The present invention may alternately be described as an apparatus for patient treatment including:
 a housing with a side wall;
 a first window in the side wall;
 an optical fiber having a tip, the first window positioned such that light may pass between the tip and a light communicating part of the first window; and
 lengthwise offset first and second electrodes mounted to the side wall and operable for detecting the presence of conductive cardiac tissue; and
 wherein the first and second electrodes have contact surfaces which are limited to an angular range excluding at least a back part of the side wall radially opposite the first window.

The present invention may alternately be described as a method of patient treatment with the steps of:

inserting an apparatus at least partly in a patient, the apparatus having:
an outer catheter having a proximal end and a distal end having at least a first passage extending lengthwise therein;
an inner catheter disposed at least partly in the first passage and having a proximal end and a distal end, the inner catheter having a side wall, a first window in the side wall, and an optical fiber having a tip, the first window positioned such that light may pass between the tip and a light communicating part of the first window, the inner catheter having an extending portion extendable out the distal end of the outer catheter by a variable amount;
lengthwise offset first and second electrodes, the first electrode mounted on an external surface of the side wall and the second electrode mounted on a surface selected from the group consisting of: the external surface of the side wall and an external surface of the outer catheter, the first and second electrodes operable for detecting the presence of conductive cardiac tissue; and
a steering means for steering the outer catheter;
using the steering means to position the distal end of the outer catheter at a desired location within the patient;
extending the extending portion of the inner catheter, while an anchor point on the outer catheter remains stationary; and
using the steering means to pivot the distal end of the inner catheter relative to the anchor point.

The present invention may alternately be described as a method of patient treatment with the steps of:

inserting a catheter at least partly within a patient, the catheter having:
a housing with a side wall;
a first window in the side wall;
an optical fiber having a tip, the first window positioned such that light may pass between the tip and a light communicating part of the first window;
lengthwise offset first and second electrodes mounted to the side wall and operable for detecting the presence of conductive cardiac tissue; and
a steering means for steering the catheter including a spring means for bending the catheter;
using the steering means to position a distal end of the catheter at a desired location within a patient's heart such that the spring means is bent so as to push a distal portion of the catheter against a wall of the patient's heart and thus maintain the first and second electrodes in contact with the wall of the patient's heart, even during all parts of the heart beat.

BRIEF DESCRIPTION OF THE DRAWINGS

The above and other features of the present invention will be more readily understood when the following detailed description is considered in conjunction with the accompanying drawings wherein like characters represent like parts throughout the several views and in which:

FIG. 1 shows a simplified perspective view of a first embodiment of the present invention with a block diagram of a laser;

FIG. 2 shows a cross section view taken along lines 2—2 of FIG. 1;

FIG. 3 shows a cross section view with parts broken away of an outer catheter;

DETAILED DESCRIPTION

Figure 4:
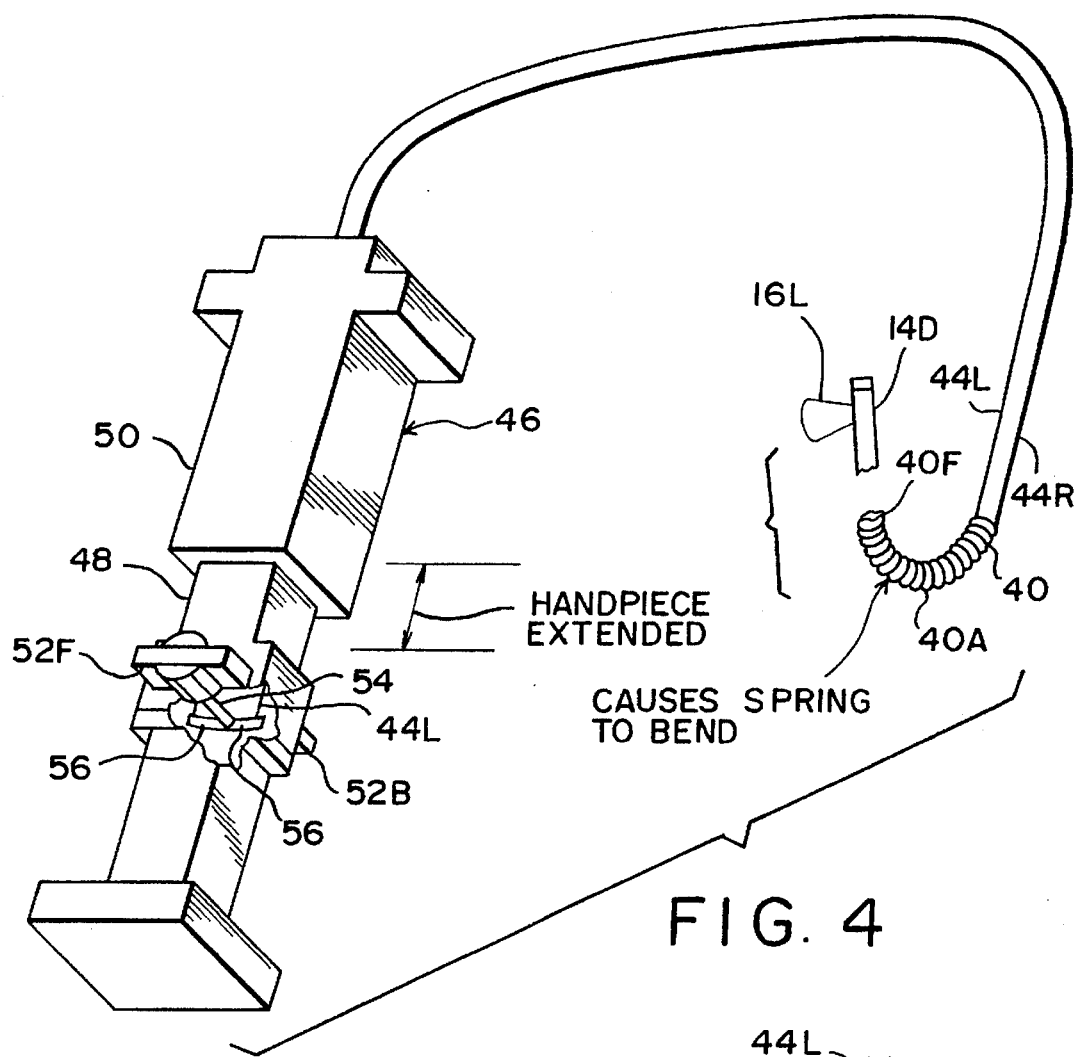
FIG. 4 shows a perspective view of a controller and associated components used with the present invention.

With reference now to FIG. 1, a catheter system or catheter 10 according to the present invention will be described. The catheter 10 includes an outer or introducer catheter 12 and an inner catheter 14. The inner catheter 14 is preferably a dual hood laser catheter built in the manner discussed and shown in the incorporated by reference Abela et al '265 patent with possible modifications as hereafter discussed. Among other differences, the optional tube and guide wire of the incorporated by reference patent would usually not be used in the design of inner catheter 14 since positioning of the inner catheter 14 will be accomplished by positioning of the outer catheter 12 in the manner discussed in more detail below.

The inner catheter 14 has a window 16 through which laser energy 16L may be applied to tissues, such as cardiac tissues, of a patient (tissues and patient not shown). More specifically, the first window 16 would be an opening through which the laser energy 16L passes and through which a flushing solution 16F is sprayed. The flushing solution 16F will have been injected into a proximal end 14P of the inner catheter 14 by supplying the flushing solution to input port 18P of a relatively standard Y connector 18. First and second ring electrodes 20F and 20S are disposed on the external surface of the cylindrical side wall 14C of inner catheter 14. The ring electrodes 20F and 20S are used for sensing cardiac conduction tissue in a manner described in more detail in the three incorporated by reference patents.

Although the inner catheter 14 may be constructed substantially identically to the catheter designs disclosed in the incorporated by reference Abela et al '265 patent, the inner catheter 14 of the present invention would generally have only a single or first window 16 for applying the laser energy 16L. The window 16 would be an opening in the side wall 14C. An optical fiber 22 carries laser energy from laser 24 into the proximal end 14P of inner catheter 14, the optical fiber 22 having a tip located adjacent to the window 16 such that laser energy supplied by laser 24 is carried out the window opening 16 as energy 16L. Although not shown, a rotational coupling unit could be used to allow fiber 22 to rotate relative to laser 24 while maintaining a beam from the laser in alignment with the entry end of the optical fiber. As shown, the distal end 14D of inner catheter 14 may include a first portion 14F having the same cylindrical configuration and diameter throughout the inner catheter 14 from ring electrode 20F to the entry location of optical fiber 22 illustrated schematically. Optionally, the inner catheter 14 may include a second section 14S, which is cylindrical and has a larger diameter than section 14F. The second section 14S may have the same outer diameter as the outer diameter of outer cathode 12. The second section 14S could be a separate piece of catheter side wall material adhered or otherwise fixed to portion 14F or, alternately, the same side wall tube making up portion 14F may simply have an enlarged outer diameter for the section 14S. The materials used for sections 14S and 14F, and also used more generally for inner catheter 14 and outer catheter 12, may be any of various catheter materials described in the incorporated by reference patents and/or other materials commonly used for catheters.

A third electrode ring 20T is mounted on the distal end 12D of outer catheter 12. Wires (not shown) may extend from rings 20F and 20S through inner catheter 14 and a similar wire (also not shown) may extend within outer catheter 12 such that all three of the electrode rings 20F, 20S, and 20T may be connected to an electrocardiographic monitor (not shown) for detection and localization of the conduction tissue. Note that three electrode rings are illustrated, but one might alternately use a single ring electrode on the inner catheter 14 and a second ring electrode such as 20T on the outer catheter 12. Although having a ring electrode such as 20T on the outer catheter 12 is not necessary for all embodiments of the present invention, it is a highly advantageous and important aspect of numerous embodiments of the present invention. In particular, it allows a variation in distance between the ring electrode 20T and one or more ring electrodes, such as 20F and 20S, which are mounted to the inner catheter 14.

The technique for varying the distance between ring electrode 20T and either or both of the ring electrodes 20F and 20S will be discussed in more detail below, but it may be noted that the inner catheter 14 may slide or translate lengthwise (extending and retracting) as indicated schematically by the arrows 28T. Additionally, the inner catheter 14 may rotate relative to outer catheter 12 as indicated by the generally circular arrows 28R. By having the inner catheter 14 rotatable and translatable (extendable) relative to the outer catheter 12, one can position an anchor point 12A within a patient's heart and then rotate and/or extend inner catheter 14 relative to outer catheter 12 in order to map a relatively large portion of the patient's heart in order to locate conduction tissue (heart not shown in FIG. 1). Likewise, once a point, such as point 12A of outer catheter 12 is anchored within a patient, movement of inner catheter 14 relative to outer catheter 12 may be used to position inner catheter 14 over a relatively wide area in order to apply laser energy for ablation of cardiac tissues. Further, although the point 12A would be anchored or relatively stable within the patient, portions of the outer catheter 12 between point 12A and part 14C of inner catheter 14 may be moved in a manner discussed below so that mapping and/or ablation can be carried out over a relatively wide zone without movement of the point 12A.

In order to realize the translational or extension movement of 28T of the distal end 14D of inner catheter 14, the proximal end 12P of outer catheter 12 would be secured in position by a clamp (not shown) or similar mechanism. This causes the proximal end 14P of inner catheter to be translated (slide lengthwise) as indicated by arrows 30T. If desired, the proximal end 14P of inner catheter 14 may include various circumferential indicia markings 32 along with corresponding numbers or letters (not shown) such that one can easily tell how far the inner catheter 14 has been extended relative to the outer catheter 12. For example, the indicia 32 could be read against the proximal edge 34 of the outer catheter 12. For ease of illustration, FIG. 1 has shown the proximal edge 34 of outer catheter 12 ending before the outer catheter 12 has reached the connector 18. If constructed in that fashion, the connector 18 would be fixed to the inner catheter 14 at its proximal end portion 14P. However, in practice the outer catheter 12 may have its proximal end 34 fixed or anchored to the connector 18, in which case the connector 18 would be fixed relative to the outer catheter 12 and would allow the inner catheter 14 to rotate and translate with respect to it. In that case, the connector 18 would supply flushing solution to the circumferential space between the inner catheter 14 and the inside wall surface of the outer catheter, the flushing solution exiting at the distal end of outer catheter 12 where the inner catheter 14 exits therefrom. (The flushing solution prevents blood from passing from the distal end to the proximal end in the gap between the outer surface of inner catheter 14 and the inner surface of outer catheter 12.) If the connector 18 is fixed to outer catheter 12, the indicia 32 would instead by disposed at position 32A and could be used for settings by using the back wall 18B of connector 18. In that case, a separate Y-connector (not shown) could be used to supply flushing solution to the inner catheter 14.

By rotating the proximal portion 14P of inner catheter 14 as indicated by generally circular arrows 30R, the distal portion 14D of inner catheter 14 will rotate as shown by arrows 28R relative to the distal portion 12D of outer catheter 12. In order to relatively precisely determine the rotational angle of inner catheter 14 relative to outer catheter 12, a marker line 36 may extend lengthwise along a part of portion 14P and numerals or letters (not shown), such as angular markings may be read adjacent to circumferentially spaced lengthwise extending indicia 38 on the proximal portion 12P of outer catheter 12. The cooperating angular indicia 36 and 38 are shown for the construction where the proximal edge 34 ends before the connector 18. In the alternate arrangement where the connector 18 is fixed relative to the outer catheter 12, lengthwise extending marker 36A may determine angular position by radially extending indicia 38A on the back wall 18B of connector 18.

With reference now to the cross section view of FIG. 2, in which the inner catheter 14 has been deleted for ease of illustration, it will be appreciated that the outer catheter 12 has a generally hollow passageway 12H in which the inner catheter 14 (not shown in FIG. 2) would be free to translate and rotate corresponding to the movements 28T and 28R respectively of FIG. 1. In order to facilitate that sliding and rotation, hydrophilic lubricants (not shown) would be coated on the outer wall of inner catheter 14 and/or the inner surface of outer catheter 12.

As shown in FIG. 1 and FIG. 2, a coiled spring 40 is disposed along a portion of outer catheter 12. The spring 40 would be at or near the distal edge (in line with ring electrode 20T in FIG. 1) of the outer catheter 12. The spring 40 is closer to that distal edge than it is to the proximal edge 34, meaning that all points on the spring 40 are closer to the edge at ring electrode 20T than the distance from any point on the spring 40 to the proximal edge 34.

With reference momentarily to FIG. 3, the outer catheter 12 is shown in cross section with spring 40 centered along the lengthwise axis 12X of outer catheter 12. As shown, the spring 40 may be captured within an increased diameter portion 42D of the catheter 12, the increased diameter portion 42D having a circumferentially extending step edge 42E at each end of spring 40 (only one end of spring 40 shown in FIG. 3). By having the spring 40 captured within an increased diameter portion 42D, the ability of inner catheter 14 to move within outer catheter 12 will be maintained without interference from the spring 40. The spring 40 may optionally have one or more of its coils, such as back coil 40B, fixed to the inside wall 12N of outer catheter 12.

Referring back to FIG. 2, right and left control wires 44R and 44L, which would be secured to one or more coils of spring 40 adjacent to the distal end of the spring 40, are used to bend spring 40 and to control it. By bending the spring 40 and controlling its position, this will in turn control the bend and positioning of outer catheter 12. Controlling outer catheter 12 in this fashion will in turn move the distal end 14D of inner catheter 14 in a manner described below. The control wires 44R and 44L are circumferentially spaced around the spiral of the coil spring 40 by 90° to 150°, preferably 105° to 135°. Even more preferably, the range of angular separation between control wire 44R and control wire 44L would be 115° to 125°, with 120° being the preferred value.

Turning now to FIG. 4, the manner of controlling the control lines 44R and 44L will be discussed. For ease of illustration, FIG. 4 simply shows a part of the distal portion 14D of the inner catheter 14 with the output laser energy 16L indicated, but with the remainder of the inner catheter 14 not illustrated. Likewise, for ease of illustration, the outer catheter is not shown in FIG. 4 so that the spring 40 and control lines 44R and 44L are more easily viewed. A controller 46 serves as a control means for bending the coil spring 40 by manipulating the control lines 44R and 44L. The controller 46 includes a sliding assembly 48 which may slide relative to a base portion 50. The wires or control lines 44R and 44L are attached to a part of the slide assembly 48. The slide assembly 48 may be considered as a hand piece which can be extended and retracted as shown for the hand piece extended arrows in FIG. 4. By extending hand piece or slide assembly 48 downward relative to base 50 in FIG. 4, both control lines 44R and 44L are pulled to cause point 40F of spring 40 to be folded or bent back towards the spring in the manner shown in FIG. 4. Point 40F is seen in FIG. 2 to be midway between control lines 44R and 44L. As shown in FIG. 4, sufficient pulling on the control lines 44L and 44R will cause the spring 40 to fold into a U shape. Less or reduced movement of hand piece 48 relative to base 50 may result in a J or similar shape.

Continuing to view FIG. 4, the hand piece or slide assembly 48 includes identical front and back control knobs 52F and 52B having a shaft 54 connected to rotate with the control knobs 52F and 52B. The shaft 54, only a portion of which is shown, has arms 56 fixed on opposite sides thereof, each control line 44R and 44L connected to a corresponding one of the arms 56. Upon rotating the control knob such as 52F, the arms 56 rotate a corresponding amount so as to increase the pull on one of the control lines and decrease the pull on the other of the control lines.

Figure 5A:
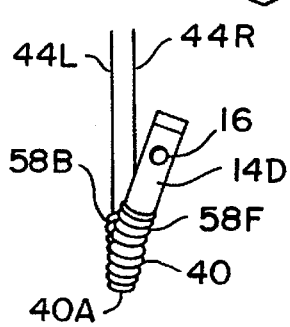
FIGS. 5A, 5B, and 5C are simplified operational diagrams illustrating the relationship between a control knob and the distal end of the catheter when the control knob is in three different positions.
Figure 5A:
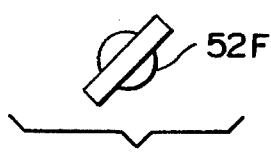
Figure 5B:
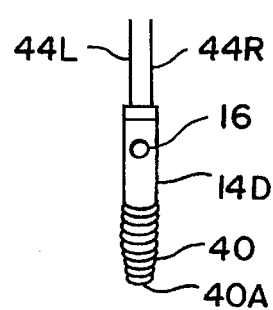
Figure 5B:
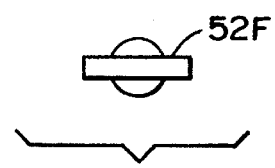
Figure 5C:
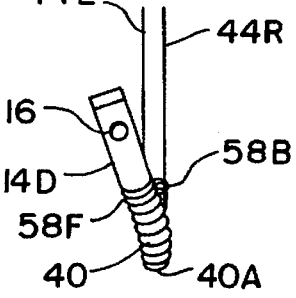
Figure 5C:

The effect of rotating the control knob 52F will be better understood with reference to FIGS. 5A, 5B, and 5C. With the control knob 52F in the position of FIG. 5B, both control lines 44R and 44L will be retracted by the same amount resulting in the orientation illustrated for the distal end 14D of the catheter. In that position, the outer catheter 12 (not shown in FIG. 5B for ease of illustration), as well as the inner catheter 14, would have a bend corresponding to spring 40 of FIG. 5B, which bend lies in a vertical plane (not separately shown) perpendicular to the plane of view of FIG. 5B and centered intermediate the portion of control lines 44R and 44L as illustrated. Basically, the bend associated with coil spring 40 defines a plane in the position of FIG. 5B.

Upon counterclockwise rotation of control knob 52F from its FIG. 5B position to assume its FIG. 5A position, the bend associated with coil spring 40 is not planar. Instead, a front portion 58F of coil spring 40 is out of the plane corresponding to a back portion 58B of the coil spring 40. In like fashion, the bend in the outer catheter 12 (not shown in FIG. 5A) and the bend in inner catheter 14 would have a configuration corresponding to that of coil spring 40. In other words, each of those bends in the inner catheter 14 and outer catheter 12 would be non-planar.

Upon rotating the control knob 52F clockwise from its FIG. 5A position to its position illustrated for FIG. 5C, the front part 58F of coil 40 moves relative to the back part 58B of coil spring 40 in the manner shown. By turning the control knob 52F between its FIG. 5A position and its FIG. 5C position, the distal end 14D of inner catheter 14 moves back and forth in a similar motion to a windshield wiper on a car. Note that a point 40A on coil spring 40 is essentially stationary throughout the positions of FIGS. 5A, 5B, and 5C as distal portion 14D pivots about point 40A. The point 40A is also illustrated in FIG. 4 and will be understood as being immediately inside the anchor or stationary point 12A of FIG. 1. The point 40A would be essentially midway through the 180° bend in coil spring 40.

By combining the present invention's ability to place point 12A (refer back to FIG. 1) corresponding to point 40A in FIGS. 4, 5A, 5B, and 5C in a relatively stationary position within a patient, with the ability to provide three different types of movements of distal portion 14D of inner catheter 14, a relatively large area or zone within a patient's heart can be mapped for conduction tissue and/or ablated relatively quickly and efficiently. Specifically, the controller 46 of FIG. 4 provides the back and forth or windshield wiper type movement illustrated in FIGS. 5A through 5C, whereas translation 30T and rotation 30R (refer back to FIG. 1) provide corresponding extension 28T and rotation 28R of the distal portion 14D.

The three types of motion discussed will now be illustrated with reference to FIG. 6 and FIG. 7. However, some background information will first be presented relative to cardiac conditions which the present invention is especially well suited for. The catheter 10 of FIG. 1 may be a ventricular arrhythmia ablation catheter designed to be used to percutaneously laser-thermally coagulate arrhythmia foci in the left ventricle of the heart. Designing a catheter for this application is somewhat more difficult than designing a His Bundle (HBA) catheter, as the HBA catheter does not enter the left ventricle.

A ventricular arrhythmia focus is usually a small portion of viable myocardium which has been surrounded by scar tissue and is no longer in direct communication with the rest of the heart. A ventricular arrhythmia focus is frequently formed following a heart attack, when a portion of the heart muscle is deprived of its blood supply and dies. This infarcted muscle is replaced by fibrotic scar tissue, not by new muscle. If a small part of myocardium in the infarcted region manages to survive the heart attack, then it has the potential to become an arrhythmia focus. Half of the people who die of heart attacks die as the result of a ventricular tachyrhythmia or ventricular fibrillation which occurs when one of these arrhythmia foci starts to generate its own pacing signals and causes the heart to start to beat rapidly and uncontrollably. When the heart starts to beat very rapidly (ventricular fibrillation), its pumping efficiency falls dramatically and the arterial blood flow drops to nearly nothing.

It is difficult for cardiologists to localize ventricular arrhythmia foci in the catheterization laboratory, and currently there is not an effective catheterization technique to ablate these arrhythmia foci. The principle problem associated with ventricular mapping and arrhythmia foci ablation is stabilization of the catheter in the left ventricle. The catheters described herein (such as catheter 10) allow a cardiac electrophysiologist to accurately localize a ventricular arrhythmia focus and destroy it by applying laser energy to the site and coagulating the myocardium producing the unwanted and dangerous pacing signals. These catheters utilize the electrode guidance and dual-hood art of the incorporated by reference patents, but also have a steerable segment, different shapes, and shock-absorbing characteristics of the steerable segment, shape and catheter material. The three innovations work in combination to allow precise movement of the catheter tip inside the ventricle and to prevent the catheter tip from losing contact with the myocardium during a heart beat.

Although steerability is important, stability is the greater problem. To be useful for ventricular mapping and arrhythmia foci ablation, the catheter must maintain contact with the same portion of the myocardium during systole and diastole. These designs address the problem of stability by their shape and by the compliance of the catheter and spring. The springs such as spring 40 maintain contact between the distal portion 14D and the wall, even as the heart moves.

The importance of the continuous contact of the catheter with the myocardium cannot be understated. If the catheter were to be pushed away from the heart wall with each contraction and would jolt back into the wall with each heart relaxation, then accurate electrophysiologic mapping of the ventricle would be impossible. Furthermore, each time the catheter bumps into the heart wall, it is possible to create a premature ventricular contraction which would completely frustrate any electrophysiologic exam. With regard to ablation of ventricular arrhythmia foci, if the catheter is not in contact with the myocardium, then efficient heating is not possible and arrhythmia ablation cannot be achieved.

Currently, the catheters used for ventricular mapping bend in approximately a 90° angle and only the very tip of the catheter touches the myocardium. These catheters do not always maintain a continuous contact with the heart wall. They have no shock-absorbing element (unlike the present invention's use of shock absorbing spring 40) and are frequently jolted away from the wall during a ventricular contraction. Furthermore, these catheters have been used with radio frequency (RF) energy for ventricular arrhythmia ablation and have not met with much success. RF energy has a shallow depth of penetration into myocardium and is unable to coagulate tissues much deeper than 4 or 5 mm. The left ventricular wall is up to 1 cm thick, and an arrhythmia focus may occur at any location in the wall, therefore an RF ablation technique would not be able to ablate a focus deep in the LV wall.

Figure 6:
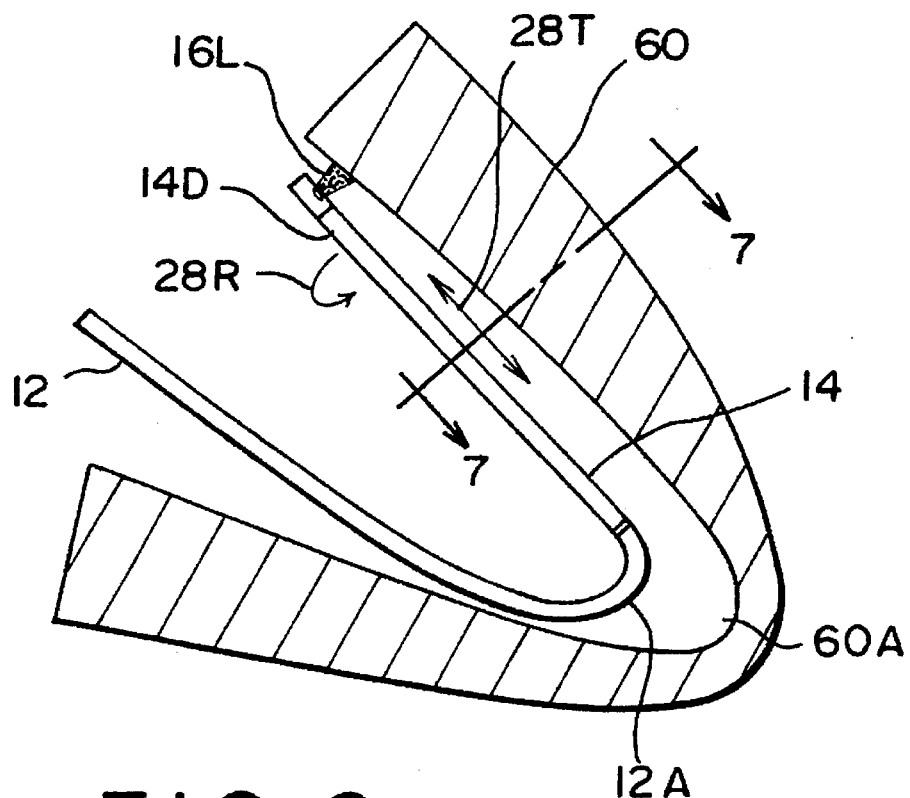
FIG. 6 shows a simplified longitudinal cross section of a patient's heart with the catheter system of the present invention in place.
Figure 7:
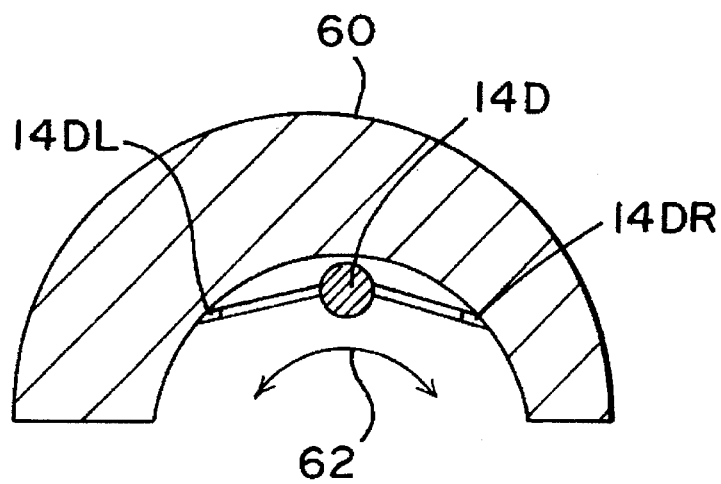
FIG. 7 shows a simplified cross section taken along lines 7—7 of FIG. 6.

With reference now to FIGS. 6 and 7, the point 12A of outer catheter 12 may be anchored in or immediately adjacent to the apex 60A of a patient's heart. The translational or extension movement 28T and rotational movement 28R of the distal end 14D of inner catheter 14 is illustrated, whereas the windshield wiper like pivoting about point 12A is illustrated by the difference between position 14D (corresponding to FIG. 5B) and left position 14DL of distal end 14D (corresponding to FIG. 5C) and the right position 14DR of 14D (corresponding to position of FIG. 5A), this sweeping or wiping motion illustrated by arrow 62.

Figure 8:
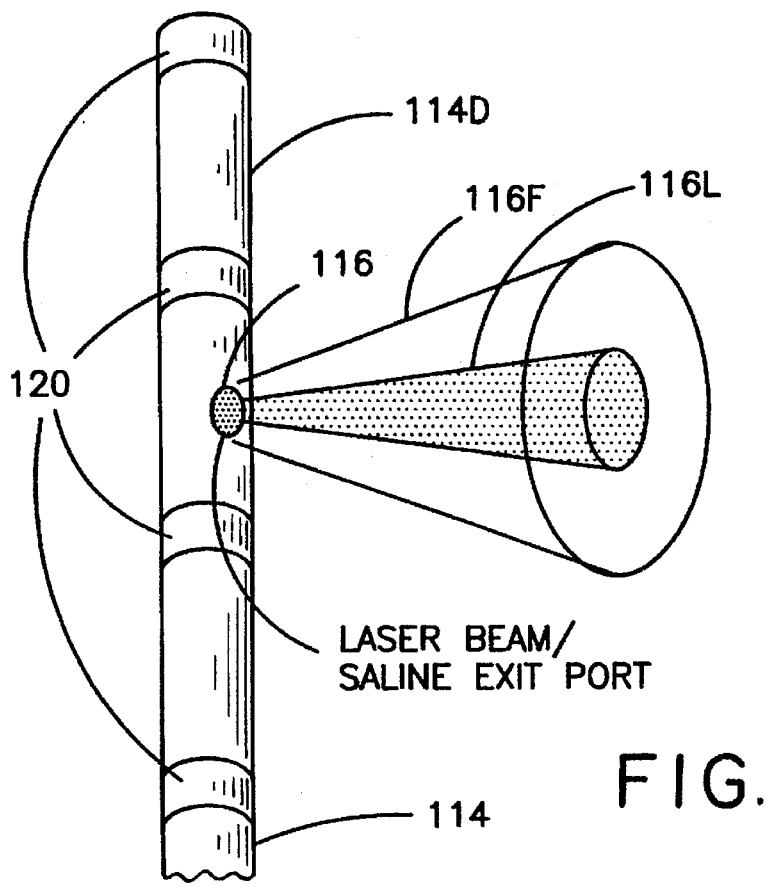
FIG. 8 shows a second embodiment inner catheter according to the present invention.

Turning now to FIG. 8, a distal end 114D of a quadripolar ablation catheter 114 is shown. The catheter 114 may be an inner catheter cooperating with an outer catheter (not shown) in the same manner as discussed with respect to the embodiment of FIGS. 1–7. Alternately, the ablation catheter 114 may be used without regard to an outer catheter. The components of the catheter 114 are labeled in the 100 series with the same last two digits as the corresponding component, if any, of the embodiment of FIGS. 1–7. (In similar fashion, all other embodiments will have the same last two digits as corresponding components from the embodiment of FIGS. 1–7.) For the embodiment of FIG. 8, as well as further alternate embodiments discussed below, components will be structured and operate in the same fashion as the corresponding component in the embodiment of FIGS. 1–7 except where otherwise noted. The window 116, which is an opening, allows passage of laser energy 116L and flushing solution 116F. As illustrated, the window 116 is located in the middle of four electrode rings 120. That is the window 116 is located with two electrode rings 120 on one side and two electrode rings 120 on the other side. The four electrode rings 120 may provide greater flexibility in sensing conduction tissue. If the ablation catheter 114 of FIG. 8 is used as an inner catheter an additional ring such as ring 20T (refer back momentarily to FIG. 1) may also be used to provide even greater flexibility.

Figure 9:
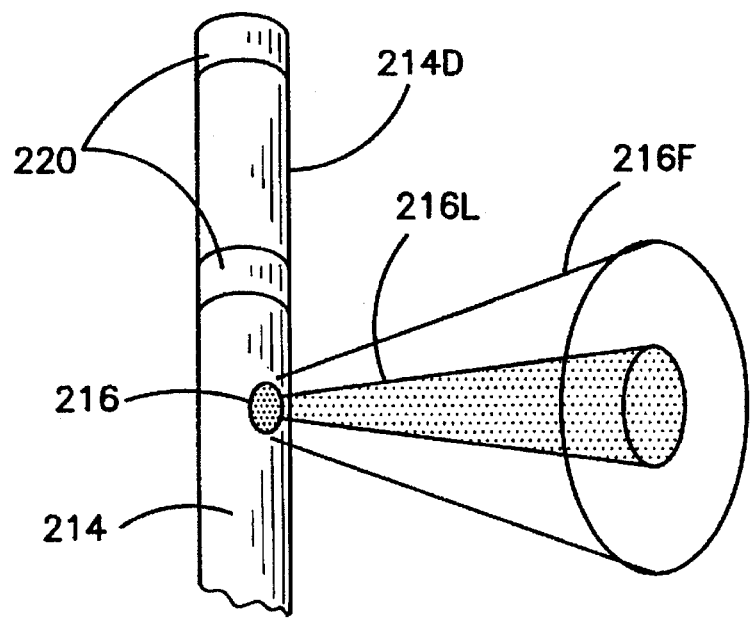
FIG. 9 shows a third embodiment inner catheter according to the present invention.

With reference now to FIG. 9, an atrial ventricular (AV) nodal ablation catheter 214 has a distal portion 214D as illustrated with a window 216 delivering laser energy 216L and saline or other flushing solution 216F. In the arrangement of catheter 214, two electrodes 220 are located on the same side of window 216. In other words, 216 is not located in the zone made up of the electrode rings 220 and the space between the electrode rings 220. The catheter 214 may, as with all other catheters disclosed herein having the last two digits of 14, be used as an inner catheter in the manner illustrated and discussed with respect to FIGS. 1–7 and, alternately, be used as a complete catheter (i.e., without use of an outer catheter like outer catheter 12 of FIG. 1). The positioning of window 216 relative to the electrode rings 220 is advantageous for treatment of AV nodes. (Other of the preferred embodiments for the inner catheter would be suited for treating abnormalities of conduction at different anatomical locations in the heart such as posterior intraventricular septum, posterior wall, and free left ventricular wall.)

Figure 10:
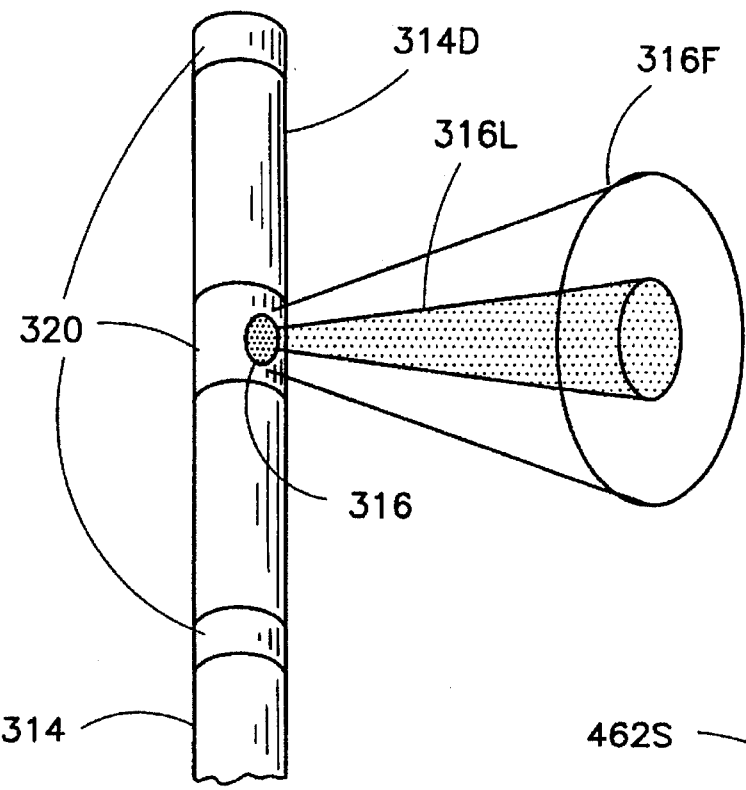
FIG. 10 shows a fourth embodiment inner catheter according to the present invention.

FIG. 10 shows an electrode exit port ablation catheter 314 wherein the distal end 314D has a window 316 located in the middle one of three electrode rings 320. Specifically, the middle ring electrode 320 may be composed of a cylindrical band of conductive material such as metal and in which a hole corresponding to the size and shape of window 316 has been drilled or otherwise made. The electrode exit port catheter 314 may be advantageous for treating certain cardiac conditions.

Figure 11A:
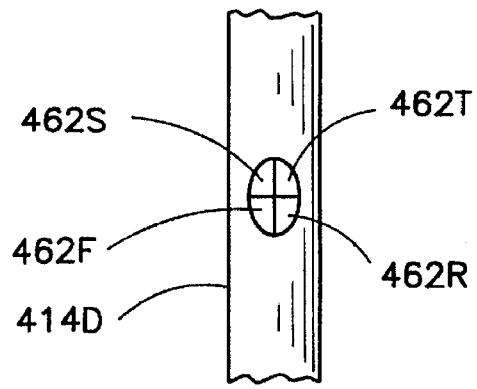
FIG. 11 shows a fifth embodiment inner catheter according to the present invention.
Figure 11:
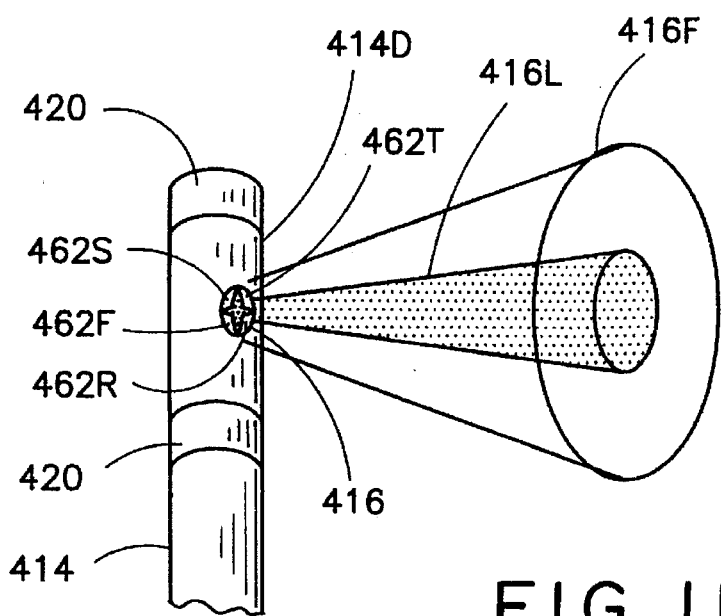

FIG. 11 shows the distal portion 414D of a catheter 414 having electrode rings 420 and a window 416 for passage of laser energy 416L and flushing solution 416F. Catheter 414 is different from catheter 14 in that the window 416 has first, second, third, and fourth rubber flaps respectively labeled 462F, 462S, 462T, and 462R. In FIG. 11, the flaps are in an open position since the flushing solution 416F has pushed them outward and open due to the pressure with which flushing solution is supplied to the interior of catheter 414. However, FIG. 11A shows each of the flaps closed such that the window 416 is closed. The flaps, made of rubber or other resilient material, may each cover one-fourth of the generally circular window 416. A greater or larger number of flaps could alternately be used and the flaps may have some degree of overlap. When the flaps are in the closed position of FIG. 11A, the pressure from blood or other bodily fluid will be blocked from entering into the catheter 414 even if no flushing solution is being applied under pressure to the interior of catheter 414. It should also be noted that the flaps 462F through 462R could utilize known techniques for making check valves so that each of the flaps may open outwardly, but may not open inwardly (towards the central lengthwise axis of catheter 414). Although it is contemplated that the pressure of saline or other flushing solution may be used to open the flaps, the flaps might also be designed to open by some other mechanical or electrical control or upon heating from the laser. If laser heating was to be used to open the flaps, each of the flaps might include a bi-metallic plate therein (not shown) which bends upon heating in known fashion.

Figure 12:
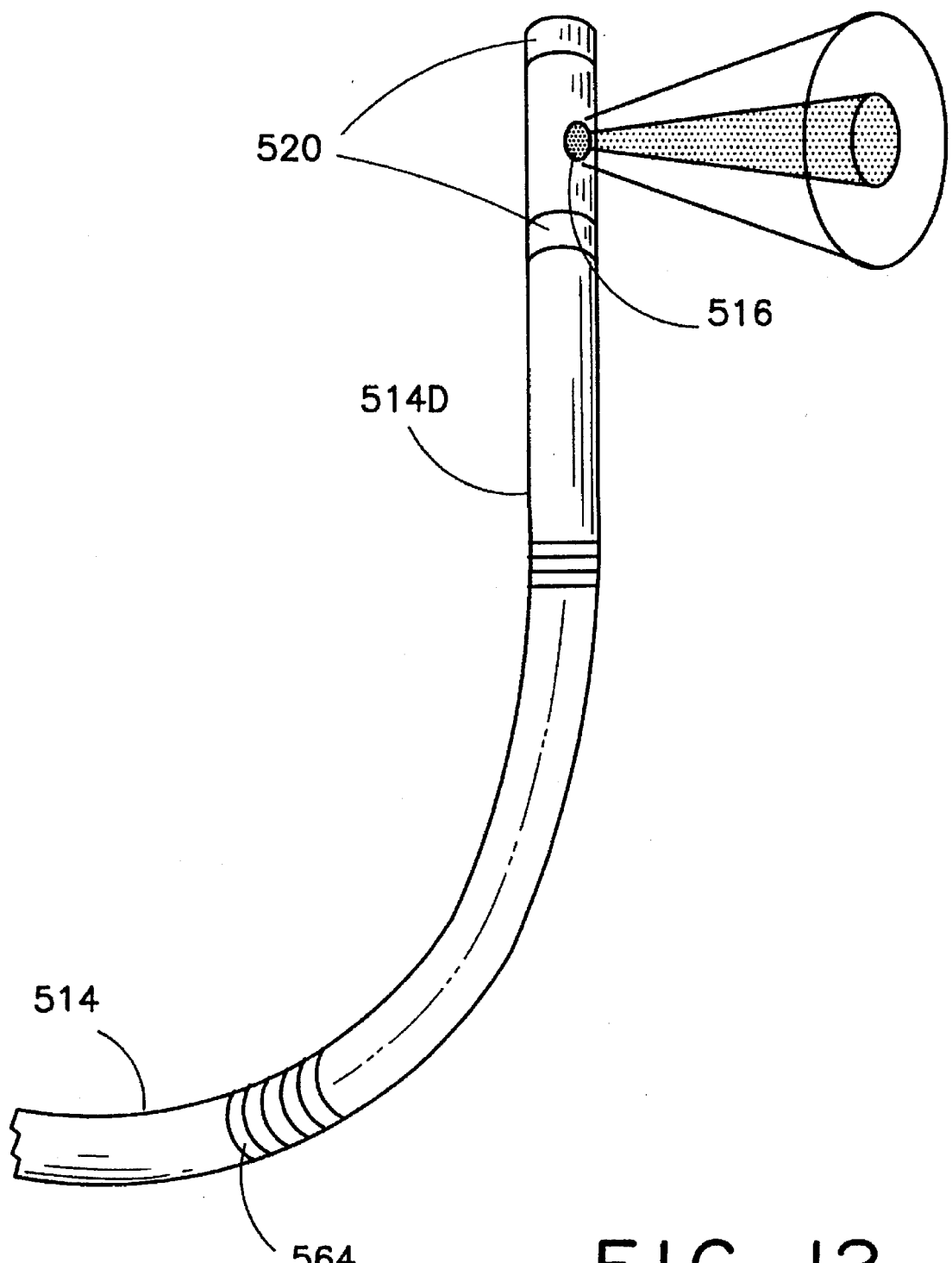
FIG. 12 shows a sixth embodiment inner catheter according to the present invention.

FIG. 12 shows an ablation catheter 514 with a window 516 and electrodes 520. Catheter 514 is different from catheter 14 in that a spring 564, only a portion of which is shown is used to steer the catheter 514. The spring 564 would be generally similar to the spring 40 of FIG. 1. However, 564 would have some of its coils (not specifically shown) secured to the outside of catheter 514. For example, several of the coils of spring 564 closest to the proximal end (not shown) of catheter 514 may be anchored to the outside of catheter 514. Although not shown, the spring 564 would have control lines similar to control lines 44R and 44L connected to one or more of the coils of spring 564 and using a controller similar to controller 46 of FIG. 4 to provide the illustrated bend. Using the same control technique discussed with respect to FIGS. 5A through 5C, the catheter 514 may provide the windshield wiper type motion depicted in those figures and illustrated as 62 in FIG. 7. The catheter 514 may provide that motion without the necessity of using an outer catheter such as 12 of FIG. 1. Spring 564 may be enclosed within a casing (not shown) or mounted within and at the inner diameter of the side wall of catheter 514 (not shown).

Figure 13:
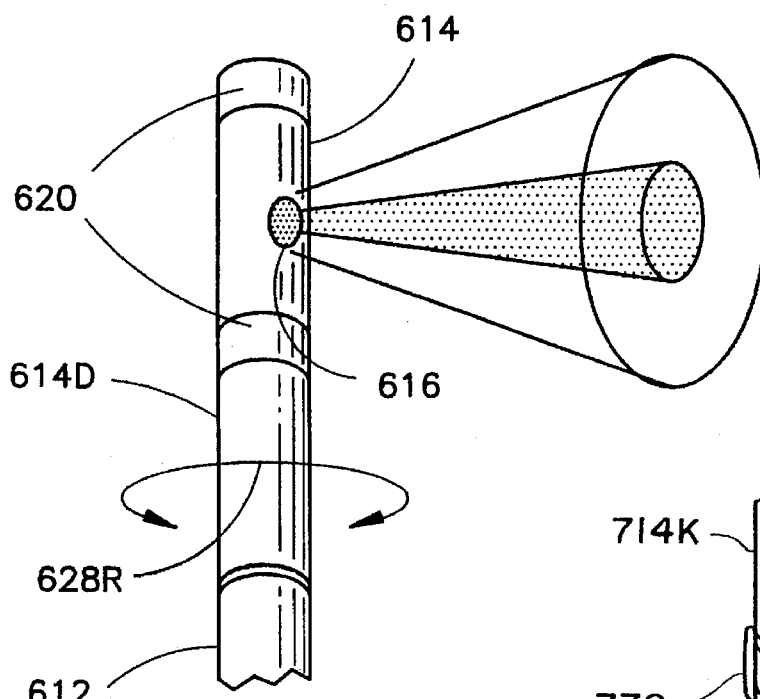
FIG. 13 shows a seven embodiment inner catheter.

With reference now to FIG. 13, an inner catheter 614 is disposed at least partly within an outer catheter 612. The outer catheter 612 is constructed identically to outer catheter 12 of FIG. 1. The inner catheter 614 has window 616 and electrode rings 620. The inner catheter 614 is constructed like the inner catheter 14 of FIG. 1 except that inner catheter 614 may rotate (as indicated by arrows 628R) relative to outer catheter 612, but may not translate or extend relative to the outer catheter 612.

Figure 14:
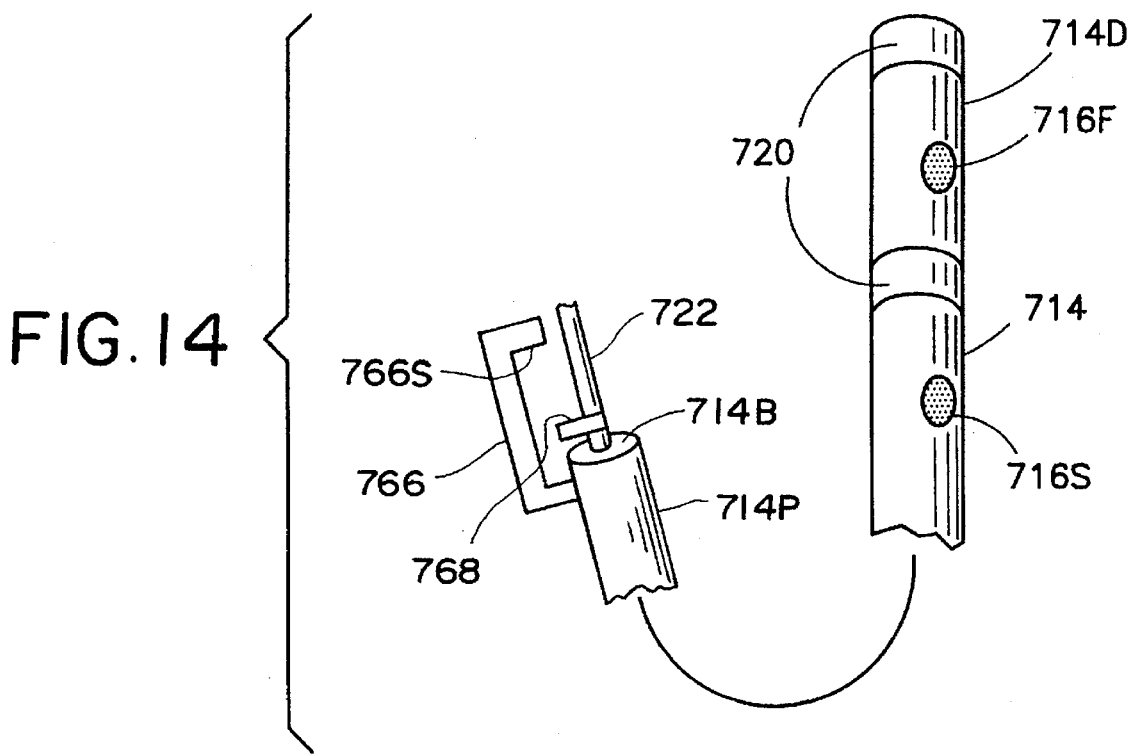
FIG. 14 shows an eighth embodiment inner catheter according to the present invention.

FIG. 14 shows the distal end 714D of a catheter 714 having two electrodes 720. Additionally, the distial portion 714D includes a first window 716F and a second window 716S, both identically constructed to the window 16 discussed with respect to FIG. 1. The two windows 716F and 716S are offset in a lengthwise direction. Additionally, FIG. 14 shows the proximal end 714P of catheter 714. As illustrated, the proximal portion 714P has a stop 766 fixed thereon. The optical fiber 722 extends out a back face 714B of the catheter 714. A member 768 is secured to the optical fiber 722. When the member 768 abuts the back surface 714B, the tip of the optical fiber 722 will be adjacent the first window 716 in order to supply laser energy out that window. The optical fiber 722 is slidably received within the catheter 714 such that pulling the member 768 pulls the optical fiber 722. When the member 768 abuts the stop surface 766S of member 766, the tip of the optical fiber 722 will be adjacent the window 716S such that laser energy may be passed through that window. This provides flexibility in the relationship between the port or opening used to supply the laser energy and the electrode rings 720.

Figure 15:
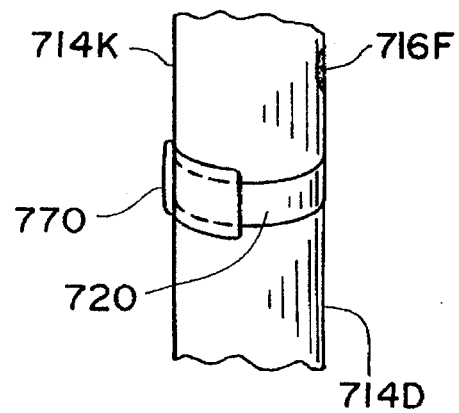
FIG. 15 is a side view of the inner catheter of FIG. 14.

With reference now to the side view of distal portion 714D in FIG. 15, a further feature of the ring electrodes 720 is illustrated. (Although only one ring electrode 720 is in FIG. 15, it will be understood that both ring electrodes 720 would be configured in the same fashion. As illustrated in FIG. 15, a part of the ring electrode 720 at the back part 714K of catheter 714 is covered by epoxy or other insulating material 770. Accordingly, only the contact surfaces of ring electrodes 720 which are not covered by the insulating material 770 will be conducting current upon contacting the patient's heart (not shown in FIG. 15). This arrangement, which may be incorporated into all of the other embodiments having ring electrodes, allows one to better insure that the window, such as window 716F of FIG. 15, is pointing towards the cardiac tissues. As illustrated in FIG. 15, the back half or 180° of the ring electrode 720 may be covered with insulating material 770. However, the portion of the ring electrode 720 which is covered with insulating material may be greater or less than 180°. The portion covered by insulating material 770 would preferably be centered radially opposite the center of the window such as window 716F. The angular extent of ring electrode 720 which is covered by insulating material 720 determines how precisely one may insure that the window 716F is facing the conduction tissue sensed by ring electrodes such as ring electrodes 720.

Figure 16:
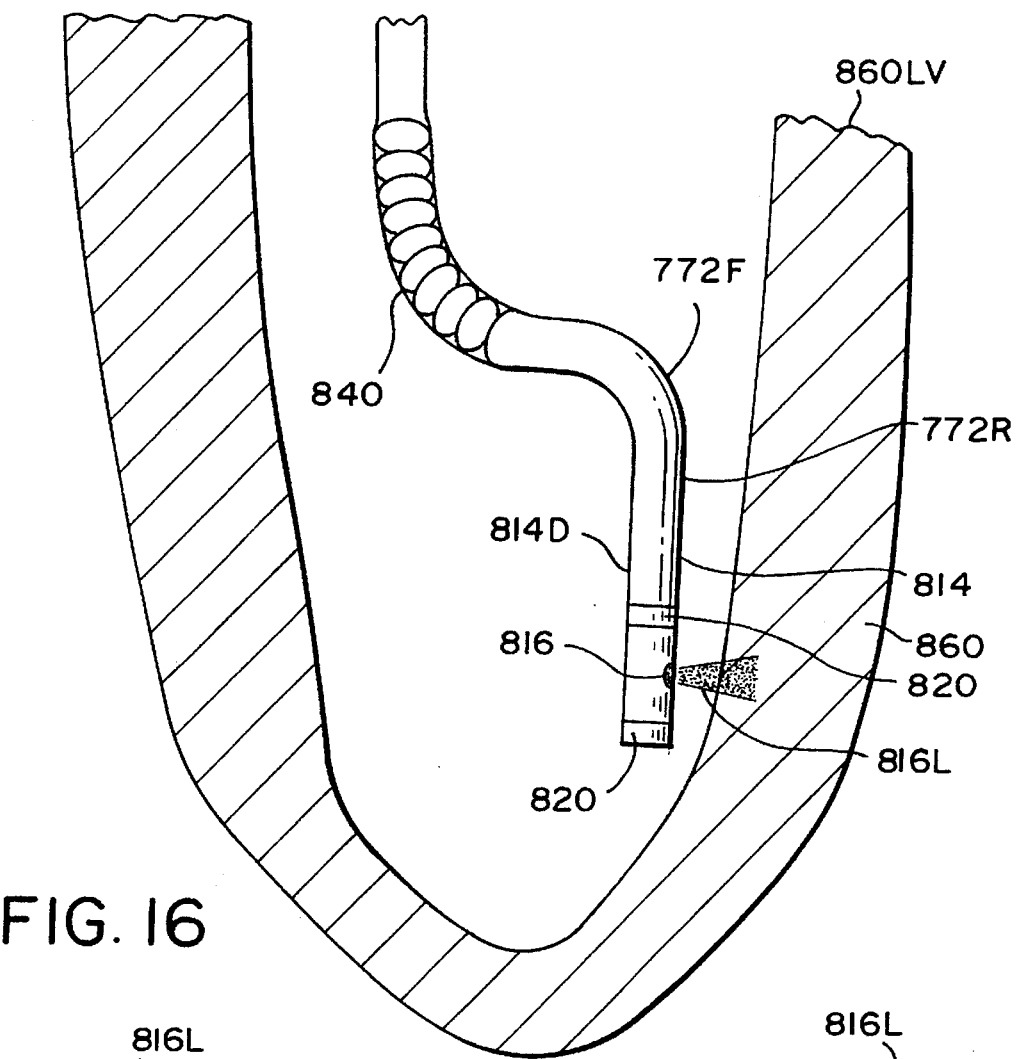
FIG. 16 is a cross-section of a patient's heart with a ninth catheter design.

With reference now to FIG. 16, a laser ablation catheter 814 is shown applying laser energy 816L from window 816 to the left ventricular wall 860LV of a patient's heart 860. The ablation catheter 814 is bent into the shape as shown by a spring 840 which may be disposed within an outer catheter (not shown in FIG. 16 for ease of illustration). The spring 840 may be attached to such an outer catheter in the manner discussed with respect to the FIG. 1 embodiment. Alternately, the spring 840 could be encased within the side wall of catheter 814. In either case, the catheter 814 has non-homogeneous flexibility with a flexible portion 772F along with a less flexible section 772R. The catheter 814 is relatively straight when initially disposed near the wall 860LV. Control lines (not shown) are used to initially bend the spring 840 in the L bend shown in FIG. 16. As the bend is placed in the catheter 814, the window 816 and electrode rings 820 maintain relatively close contact with the wall 860LV since the bend occurs in relatively flexible portion 772F and the less flexible or rigid portion 772R (which extends from portion 772F to the furthest ring electrode 820) stays in a relatively straight line. As discussed previously with respect to spring 40 of FIG. 1, the spring 840 serves as a shock absorber to maintain contact between ring electrodes 820 and the wall 860LV even when the heart is beating.

Figure 17A:
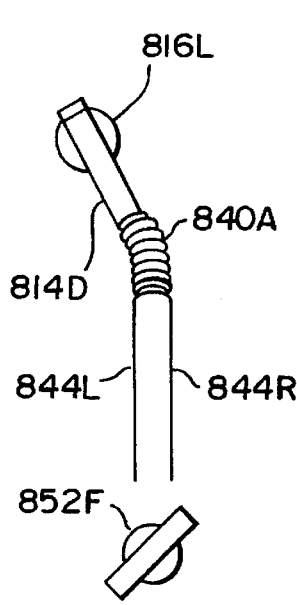
FIGS. 17A, 17B, and 17C are simplified operational diagrams illustrating the relationship between a control knob and the distal end of the catheter when the control knob is in three different positions for the catheter of FIG. 16.
Figure 17B:
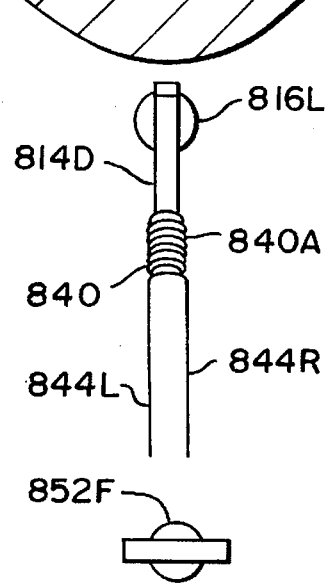
Figure 17C:
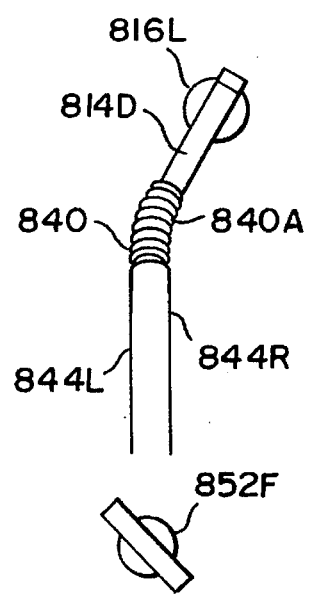

The operation of the catheter 814 of FIG. 16 will be discussed with reference to FIGS. 17A, 17B, and 17C showing different positions of a control knob 852F (which would be part of an assembly such as assembly 46 of FIG. 4) and the corresponding positions of distal portion 814D and spring 840 as control knob 852F manipulates control lines 844R and 844L. In all of the positions illustrated in FIGS. 17A through 17C, the laser energy 816L will be applied perpendicular and into the plane of view. The operation of control knob 852F to provide a windshield wiper type movement (pivoting of distal portion 814D about anchor point 840A) illustrated between FIGS. 17A and 17C is essentially the same as discussed above with respect to FIGS. 5A through 5C except that the shape of the bend in spring 840 is different and the corresponding orientation of the distal end 814D is somewhat different.

It should be readily appreciated that other steering mechanisms than that shown could be used for the outer catheter 12 of FIG. 1. Although not illustrated, an alternate arrangement of outer catheter 12 would include two passageways instead of the one passageway 12H of FIG. 2. One of the passageways would hold the inner catheter, whereas the other passageway could hold a separate steering mechanism different from that shown and discussed.

Figure 18:
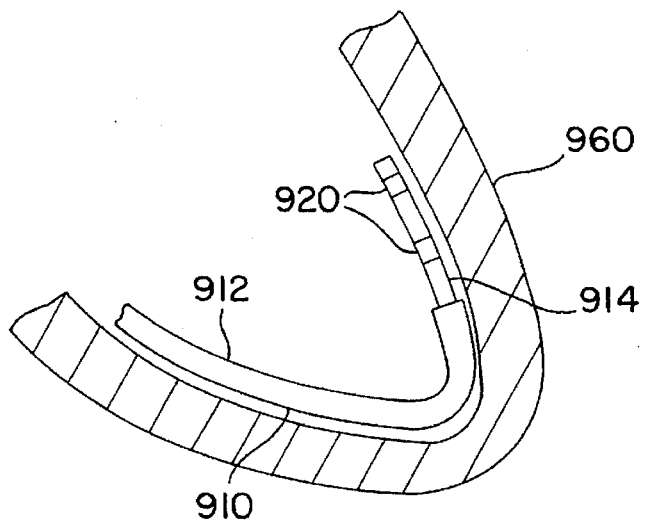
FIG. 18 shows a view similar to FIG. 6 of an alternate catheter.

FIG. 18 shows a view similar to FIG. 6 of an alternate catheter 910 with components having the same last two digits as the corresponding component, if any, of the embodiment of FIG. 6 (and related FIGS.). Catheter 910 is constructed and works in the same ways as discussed for the earlier embodiments except as discussed hereafter. Catheter 910 is in heart 960 and has an outer catheter body 912, inner catheter body 914, and electrodes 920. The inner catheter body 914 moves relative to the outer catheter body 912 to allow electrodes 920 (which could be in any of the configurations previously discussed). As used herein and similar to the terminology used throughout this application, the inner catheter body 914 may be referred to as an inner catheter and the outer catheter body 912 may be referred to as an outer catheter even through they preferably are components of a single catheter which provide windshield wiper type movement and are slidable (extendable) and rotable relative to each other and which have limits in their relative movement (such as stop 14S discussed relative to FIG. 1). Inner catheter 914 differs from the prior inner catheters in that it has no optical fiber or other ablation device. Instead, it may simply use the various movements (discussed above relative to other embodiments) for mapping of cardiac tissues. The electrodes 920, which may have any of the electrode arrangements discussed above, would touch the wall of heart 960 using any of the outer catheter anchoring techniques discussed above and below.

Figure 19:
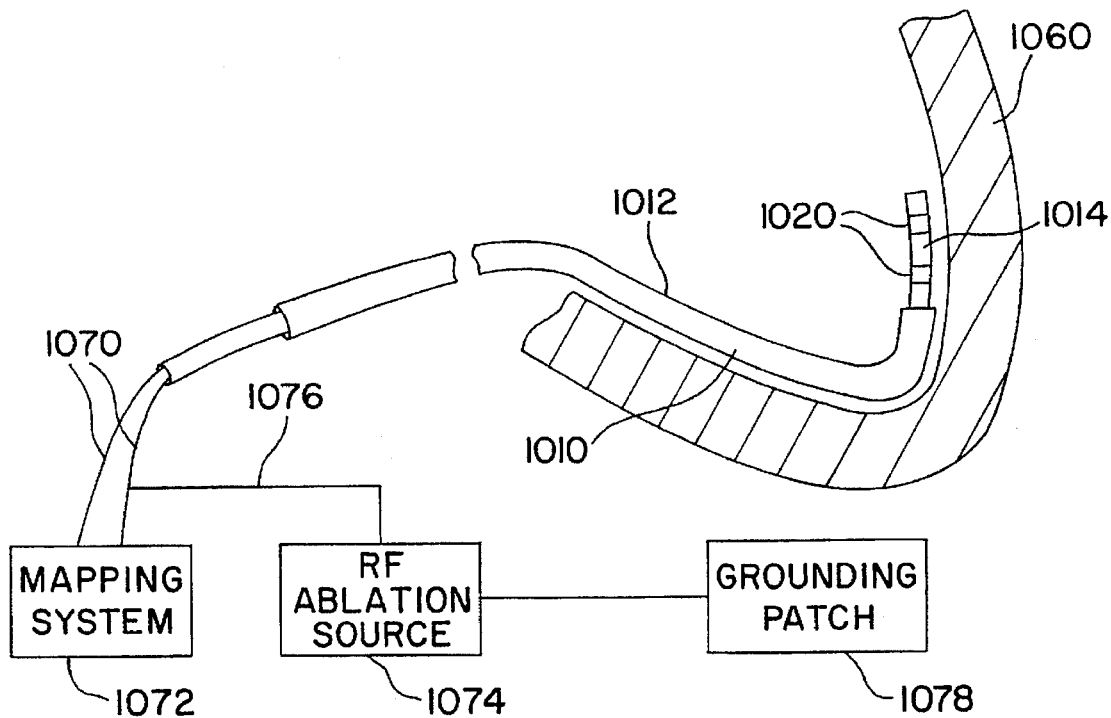
FIG. 19 shows a view similar to FIG. 6 of a further alternate catheter.

FIG. 19 shows a view similar to FIG. 6 of an alternate catheter 1010 with components having the same last two digits as the corresponding component, if any, of the embodiment of FIG. 6 (and related FIGS.). Catheter 1010 is constructed and works in the same ways as discussed for the earlier embodiments except as discussed hereafter. Catheter 1010 is in heart 960 and has an outer catheter body 1012, inner catheter body 1014, and electrodes 1020. The inner catheter body 1014 moves relative to the outer catheter body 1012 to allow electrodes 1020 (which could be in any of the configurations previously discussed). As used herein and similar to the terminology used throughout this application, the inner catheter body 1014 may be referred to as an inner catheter and the outer catheter body 1012 may be referred to as an outer catheter even through they preferably are components of a single catheter which provide the windshield wiper type movement and are slidable (extendable) and rotable relative to each other and which have limits in their relative movement (such as stop 14S discussed relative to FIG. 1). Inner catheter 1014 differs from the prior inner catheters in that it has no optical fiber for ablation. Instead, it may use the various movements (discussed above relative to other embodiments) for mapping of cardiac tissues and use one or more of the electrodes 1020 (often just the electrode closest to the distal end, but could include more than one) as a radio frequency (RF) antenna for ablation. The electrodes 1020, which may have any of the electrode arrangements discussed above, would touch the wall of heart 1060 using any of the outer catheter anchoring techniques discussed above and below. As with catheter 910, catheter 1010 could optionally have the flushing features or no flushing features and could optionally have one or more balloons for occlusion purposes, although balloons are preferably avoided since it is difficult or impossible to use them in the heart. Wires 1070 extend from electrodes 1020 to mapping system 1072, which may be any of various systems for sensing conduction tissue and otherwise mapping the heart. At least one of the wires 1070 may be connected to an RF ablation source 1074, which may be any of various systems for ablation. Source 1074 may be connected to a grounding patch 1078 in known fashion. Although not shown, one or more filters may be used in known fashion to isolate the ampping system 1072 and RF source 1074 from each other or one from the other. Further the inner catheter 1014 may alternately include or incorporate ablation techniques other than the laser and RF techniques.

Figure 20:
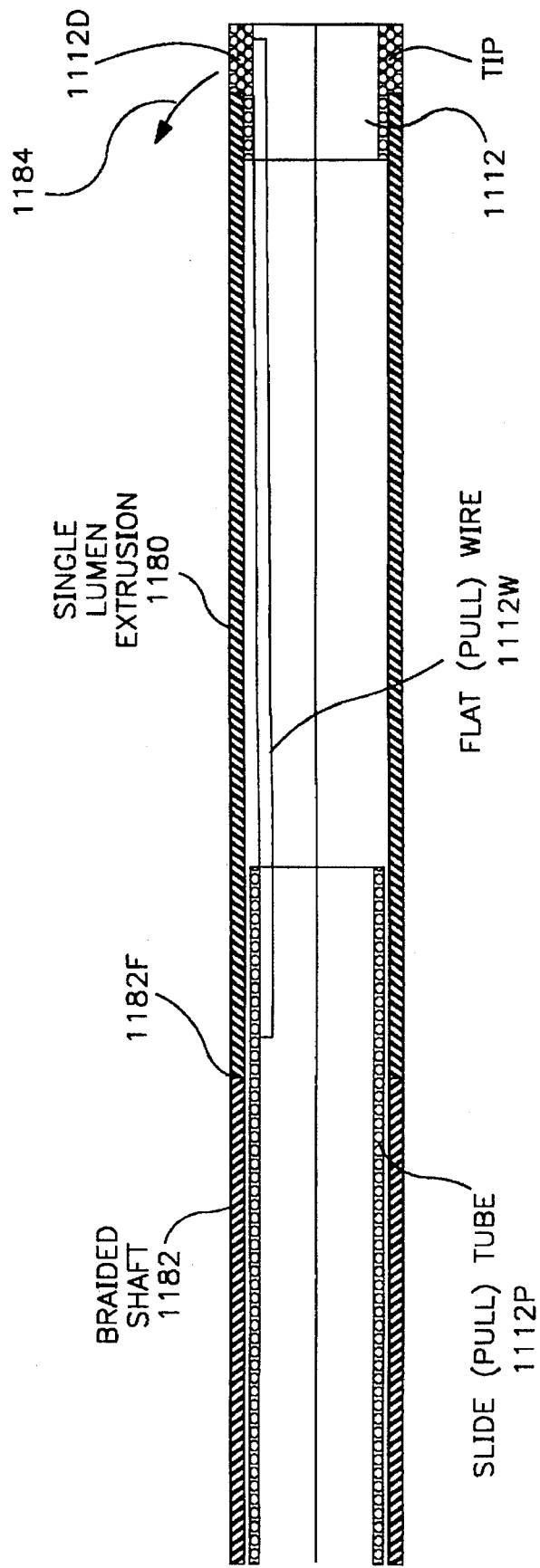
FIG. 20 shows an alternate structure for anchoring.

With reference now to FIG. 20, an alternate technique for providing the anchoring and various movements between an outer catheter body and an inner catheter body will be discussed. This figure only shows the outer catheter body 1112 and various components related to providing the anchoring. An inner catheter of any of the types discussed herein may slide within outer catheter body 1112, which body includes a distal stepped collar 1112D and a slide or pull tube 1112P connected by a relatively rigid flat metal ribbon pull wire 1112W. The stepped collar 1112D is welded or otherwise secured to a single lumen extrusion 1180 of significantly less stiffness than a stainless steel wire braid reinforced construction shaft 1182 to which it is also secured. The pull tube 1112P extends from the proximal end of the structure outside the patient (not shown) to just past interface 1182F between shaft 1182 and extrusion 1180. The shaft 1182 extends from the proximal end of the catheter outside the patient. Holding shaft 1182 stationary and pulling on the pull tube 1112P causes the extrusion 1180 and unshown inner catheter to bend in the direction of the wire as shown for bend direction 1184.

Although not shown, a handle may be attached to the proximal end of the outer catheter incorporating controls for the deflection of the outer catheter tip 1112D and extension of the inner catheter tip. The handle can be of conventional steerable electrophysiology catheter design. That is, any combination of sliding rings or rotating knobs along a tubular handle body may serve to control the deflection and extension.

Figure 21:
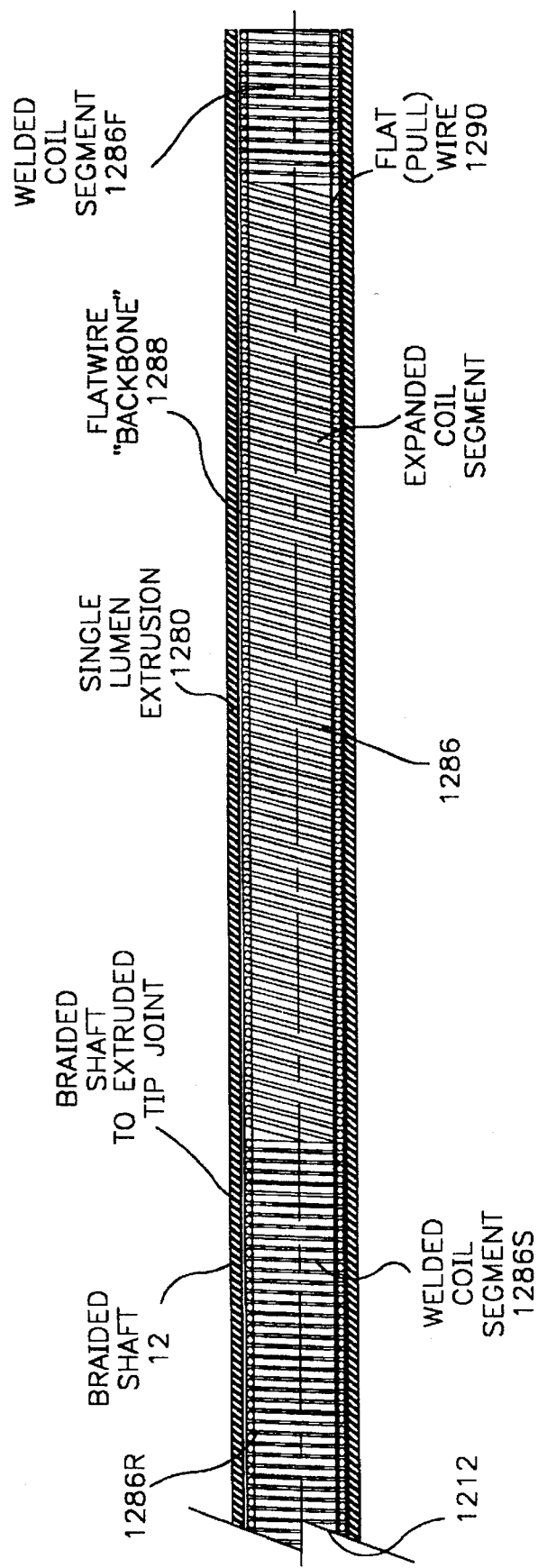
FIGS. 21 and 22 shows a structure for yet another alternate bend or anchoring technique.
Figure 22:
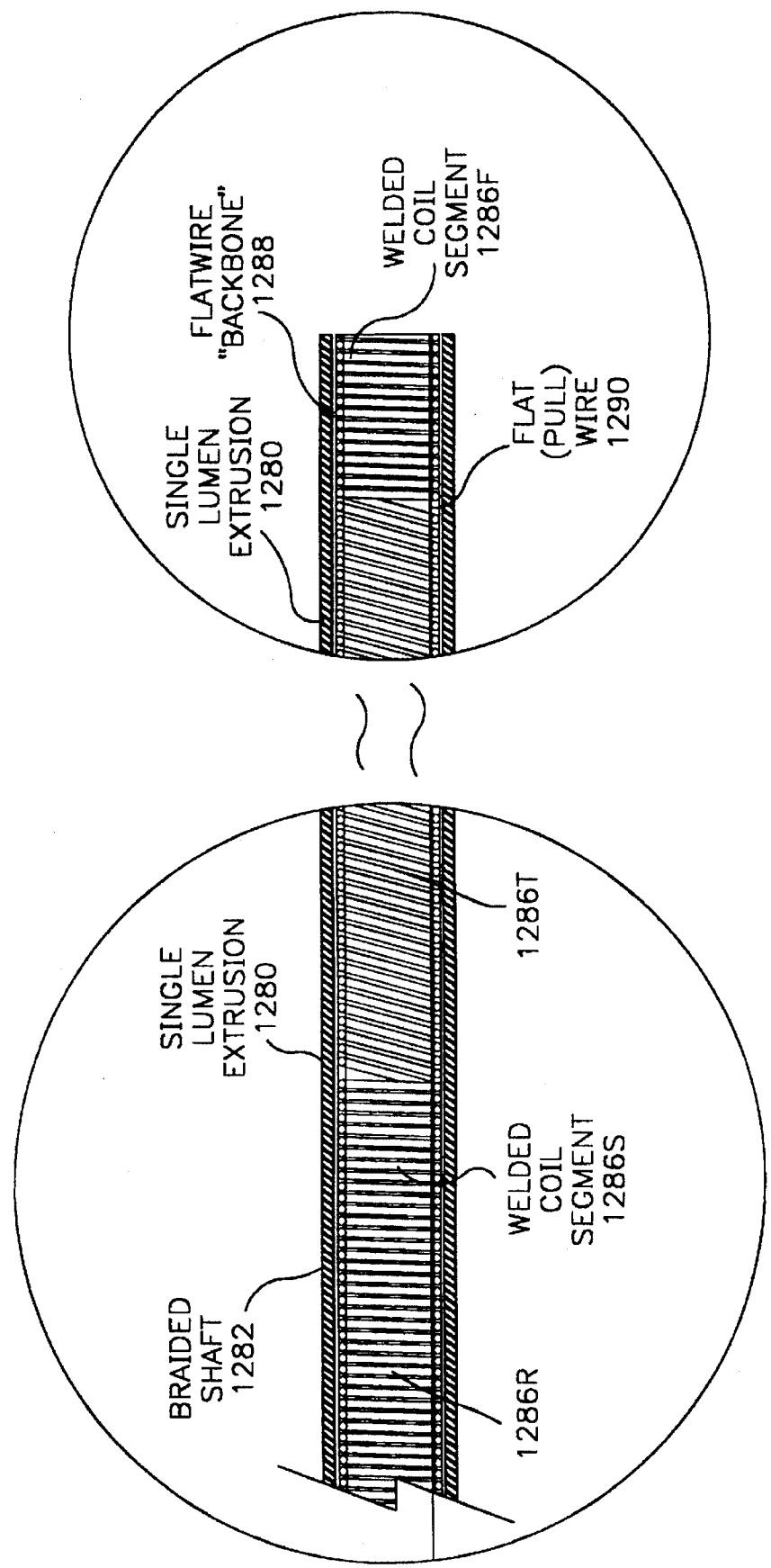

FIGS. 21 and 22 show an alternate anchoring or bend technique wherein a spring 1286 is within an outer catheter 1212. The spring 1286 has coil segments 1286F and 1286S with the coils welded together and separated by coil segment 1286T having a flat or ribbon wire backbone 1288 welded to segments 1286F and 1286S and welded to keep the coils in segment 1286T expanded somewhat. A fourth segment 1286R of the spring has close wound coils which are not welded together and not welded in an expanded state. A flat or ribbon metal pull wire 1290 is welded is attached to the distal end of the spring 1286 180 degrees (opposite side of cylinder) from the backbone wire 1288. An extrusion 1280 and braided shaft 1282 (respectively like 1180 and 1182 of FIG. 20) serve as a support for catheter 1212 and provide the torque transmission necessary to rotate the curved tip. The pull wire 1290 may be pulled at the proximal end using the techniques discussed above. Tension on wire 1290 in turn causes the tip to deflect in the direction of the pull wire. As with the embodiments of FIGS. 20 and 23, the inner catheter body is not shown, but would be constructed in the various discussed ways.

Figure 23:
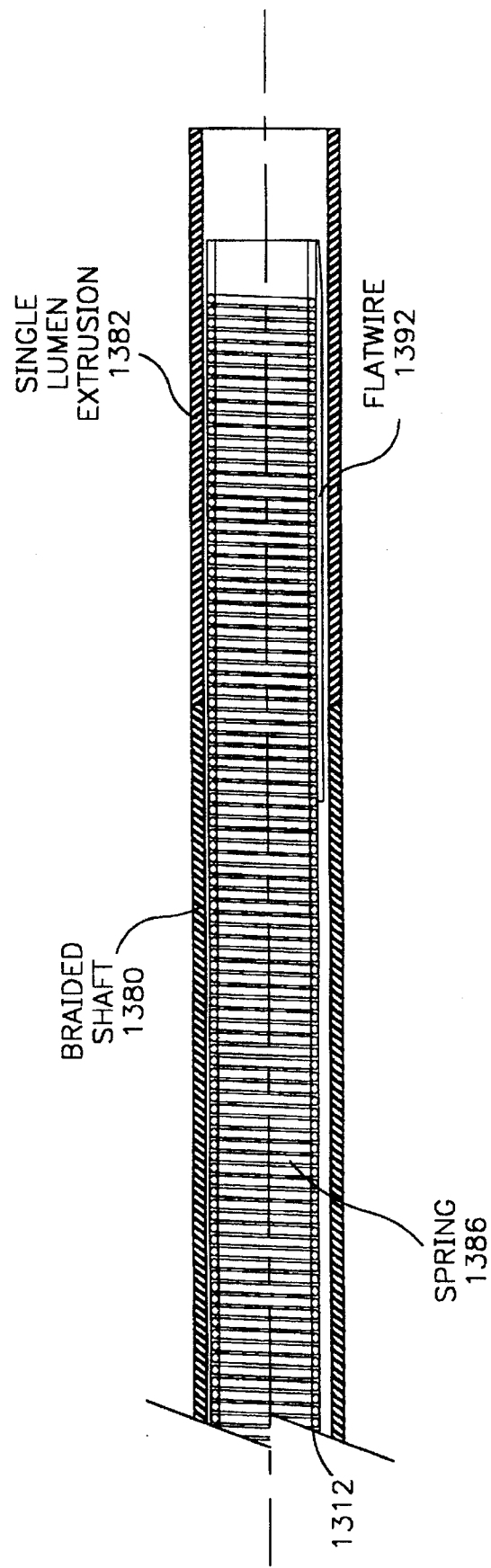
FIG. 23 shows a structure for yet another alternate bend or anchoring technique.
Figure 24:
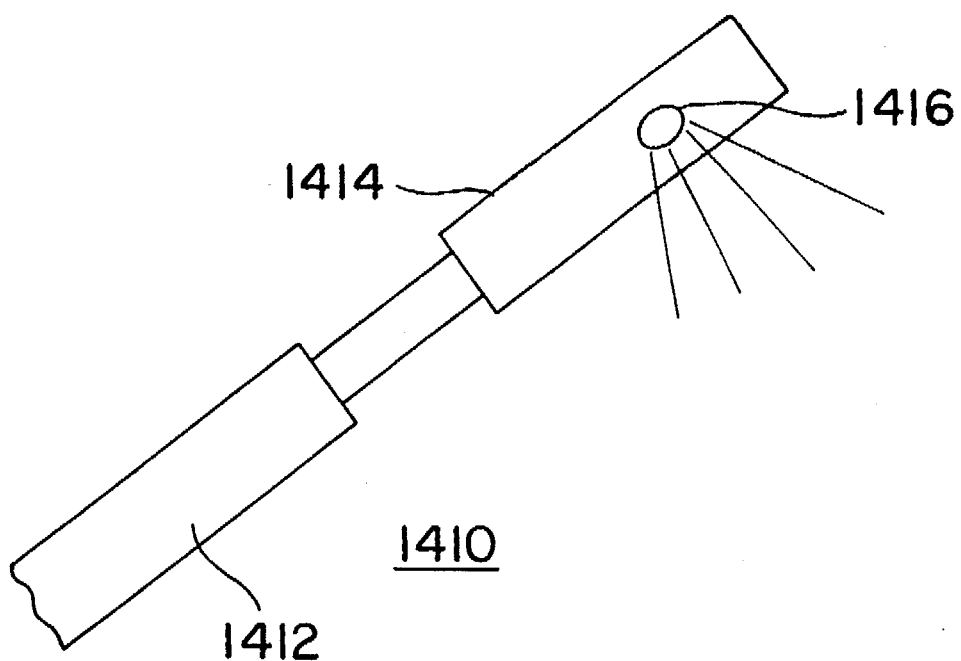
FIG. 24 shows a catheter without electrodes.

FIG. 23 shows an alternate bend or anchoring technique wherein the outer catheter 1312 is within a braided shaft 1380 and extrusion 1382 (respectively like 1180 and 1182 of FIG. 20). In this case, the outer catheter body 1312 is the same as (i.e., no tube separate from the coils) or incorporates a close wound coil spring 1386 therein. (In this case, the shaft 1380 may alternately be considered as an outer catheter body.) Although not shown, the distal end of the spring 1386 may be expanded to reduce the force required to cause the tip deflection. A flat metal ribbon wire 1392 is attached to the distal tip of the spring and anchored to shaft 1380 just proximal to the bond between the shaft 1380 and extruded tip 1382. Pushing on the spring 1386 at its proximal end outside the patient, while holding shaft 1380 stationary will cause the tip to bend in the direction of the ribbon wire.

A catheter body 1414 with window 1416 may be used with no electrodes. In other words, the catheter 1410 is constructed and operable for laser ablation in the discussed fashion, but does not have electrodes for mapping.

Although various specific constructions have been illustrated herein, it is to be understood that these are for illustrative purposes only. Various adaptations and modifications will be apparent to those of skill in the art. Accordingly, the scope of the present invention should be determined by reference to the claims appended hereto.

What is claimed is:

1. An apparatus for patient treatment comprising:
   an outer catheter having a proximal end and a distal end having at least a first passage extending lengthwise therein;
   an inner catheter disposed at least partly in said first passage and having a proximal end and a distal end, said inner catheter having a side wall, a first window in said side wall, and an optical fiber having a tip, said first window positioned such that light may pass between said tip and a light communicating part of said first window, said inner catheter having an extending portion extendable out said distal end of said outer catheter by a variable amount; and
   a steering means for steering said outer catheter.

2. The apparatus of claim 1 further comprising a second window in said side wall lengthwise offset from said first window, and wherein said optical fiber is movable between a position to pass light between said tip and said first window and a position to pass light between said tip and said second window.

3. The apparatus of claim 1 wherein said optical fiber is operable to carry laser energy to cardiac tissues of a patient, and said window is an opening for passage of light and flushing solution.

4. The apparatus of claim 1 wherein said steering means includes a coil spring mounted near said distal end of said outer catheter and a control means for bending said coil spring by manipulations at a proximal end of the apparatus.

5. The apparatus of claim 1 wherein the inner and outer catheters respectively are inner and outer parts of a single catheter and the inner part is captured to the outer part.

6. An apparatus for patient treatment comprising:
   an outer catheter having a proximal end and a distal end having at least a first passage extending lengthwise therein;
   an inner catheter movably disposed at least partly in said first passage and having a proximal end and a distal end, said inner catheter having a first window, and an optical fiber having a tip, said first window positioned such that light may pass between said tip and a light communicating part of said first window, said inner catheter having an extending portion extendable out said distal end of said outer catheter; and
   a steering means for steering said outer catheter; and
   wherein said steering means includes a coil spring mounted near said distal end of said outer catheter and a control means for bending said coil spring by manipulations at a distal end of the apparatus.

7. A method of treating a patient comprising the steps of:
   inserting a catheter at least partly within a patient, the catheter having:
      an outer catheter having a proximal end and a distal end having at least a first passage extending lengthwise therein;
      an inner catheter disposed at least partly in said first passage and having a proximal end and a distal end, said inner catheter having a first window, and an optical fiber having a tip, said first window positioned such that light may pass between said tip and a light communicating part of said first window, said inner catheter having an extending portion extendable out said distal end of said outer catheter by a variable amount;
      a steering means for steering said outer catheter; and
      wherein said outer catheter has an anchor portion; and
   using said steering means to position a distal end of said catheter at a desired location within a patient's heart such that said anchor portion of the outer catheter is secured against a wall of the patient's heart; and
   moving said inner catheter relative to said outer catheter with said anchor portion remaining in place.

8. The method of claim 7 wherein said anchor portion has a spring which bends a distal portion of the catheter against a wall of the patient's heart for anchoring.

9. The method of claim 7 further including the step of applying laser energy to the patient's heart using the optical fiber for transmission of the energy.

* * * * *